US007829336B2

(12) United States Patent
Fuchs et al.

(10) Patent No.: US 7,829,336 B2
(45) Date of Patent: Nov. 9, 2010

(54) METHOD FOR ISOLATING A SELF-RENEWING, MULTIPOTENT, SLOW-CYCLING CELL

(75) Inventors: Elaine Fuchs, New York, NY (US); Tudorita Tumbar, Ithaca, NY (US); Cedrick Blanpain, Lasne (BE); William E. Lowry, Beverly Hills, CA (US)

(73) Assignee: The Rockefeller University, New York, NY (US)

( * ) Notice: Subject to any disclaimer, the term of this patent is extended or adjusted under 35 U.S.C. 154(b) by 692 days.

(21) Appl. No.: 10/580,511

(22) PCT Filed: Nov. 12, 2004

(86) PCT No.: PCT/US2004/037925

§ 371 (c)(1), (2), (4) Date: Feb. 13, 2007

(87) PCT Pub. No.: WO2005/054445

PCT Pub. Date: Jun. 16, 2005

(65) Prior Publication Data

US 2008/0047026 A1 Feb. 21, 2008

Related U.S. Application Data

(60) Provisional application No. 60/524,466, filed on Nov. 24, 2003, provisional application No. 60/604,450, filed on Aug. 25, 2004.

(51) Int. Cl.
*C12N 5/00* (2006.01)
*C12N 5/02* (2006.01)

(52) U.S. Cl. ........................ 435/378; 435/325; 435/380

(58) Field of Classification Search ................. 435/378, 435/325, 380
See application file for complete search history.

(56) References Cited

U.S. PATENT DOCUMENTS

| | | | | |
|---|---|---|---|---|
| 5,639,618 | A * | 6/1997 | Gay | 435/7.21 |
| 5,665,557 | A * | 9/1997 | Murray et al. | 435/7.24 |
| 5,665,577 | A * | 9/1997 | Sodroski et al. | 435/456 |
| 5,861,315 | A * | 1/1999 | Nakahata | 435/384 |
| 6,485,971 | B1 * | 11/2002 | Kaur et al. | 435/371 |

FOREIGN PATENT DOCUMENTS

| | | | |
|---|---|---|---|
| WO | WO0172970 | A2 | 10/2001 |
| WO | WO02051987 | A1 | 7/2002 |

OTHER PUBLICATIONS

Strathdee et al. Gene, 229: 21-29, 1999.*
Bohl et al. Nat. Med., 3(3): 229-305, 1997.*
Mahmud et al. Blood, 97(10): 3061-3068, 2001.*
Schrieber et al. Haematologica, 94(11): 1493-1501, 2009.*
Akashi et al. Blood, 101(2): 383-390, 2003.*
Tumbar et al. Science, 303: 359-363, Jan. 2004, available online Dec. 11, 2003.*
Andressen et al., "Nestin-Specific Green Fluorescent protein Expression in Embryonic Stem Cell-Derived Neural Precursor Cells Used for Transplantation", Stem Cells 2001 19:419-424.
Song et al., "Long-Term Expression of the Gene Encoding Green Fluorescent Protein in Human Cord Blood CD34+ and K562 Cells Using Retroviral Gene Transfer", Blood 2001 98(11):p. 407b.
Bartz et al., "Large-scale isolation of immature dendritic cells with features of Langerhans cells by sorting $CD34^+$ cord blood stem cells cultured in the presence of TGF-β1 for cutaneous leukocyte antigen (CLA)", J. Immunological Methods 2003 275:137-148.
Coffin et al., "Pure populations of transduced primary human cells can be produced using GFP expressing herpes virus vectors and flow cytometry", Gene Therapy 1998 5:718-722.
Diamond et al., "Conditional Gene Expression in the Epidermis of Transgenic Mice Using the Tetracycline-Regulated Transactivators tTA and rTA Linked to the Keratin 5 Promoter", J. Invest Dermatol 2000 115:788-794.
Fujikawa et al., "Purification of adult hepatic progenitor cells using green fluorescent protein (GFP)-transgenic mice and fluorescence-activated cell sorting", Journal of Hepatology 2003 39:162-170.
Garcion et al., "Knockout mice reveal a contribution of the extracellular matrix molecule tenascin-C to neural precursor proliferation and migration", Development 2001 128:2485-2496.
Hocevar e al., "Regulation of the Wnt signaling pathway by disabled-2 (Dab2)", The EMBO Journal 2003 22(12):3084-3094.
Ivanova et al., "A Stem Cell Molecular Signature", Science 2002 298:601-604.
Jackson et al., "Stem Cells: A Minireview", Journal of Cellular Biochemistry 2002 Supplement 38:1-6.
Kanda et al., "Histone-GFP fusion protein enables sensitive analysis of chromosome dynamics in living mammalian cells", Current Biology 1998 8:377-385.
Krestel et al., "A GFP-equipped bidirectional expression module well suited for monitoring tetracycline-regulated gene expression in mouse", Nucleic Acids Research 2001 29:7e39 1-6.
Lessard et al., "Bmi-1 determines the proliferative capacity of normal and leukaemic stem cells", Nature 2003 423:255-260.
Ott et al., "Use of Recombined Embryonic Stem Cells to Isolate Neural Stem Cells", J. Cellular Biochemistry 1994 Supplement 18B:187.
Park et al., "Bmi-1 is required for maintenance of adult self-renewing haematopoietic stem cells", Nature 2003 423:302-305.
Punzel et al., "The type of stromal feeder used in limiting dilution assays influences frequency and maintenance assessment of human long-term culture initiating cells", Leukemia 1999 13:92-97.
Roy et al., "Identification, Isolation, and Promoter-Defined Separation of Mitotic Oligodendrocyte progenitor Cells from the Adult Human Subcortical White Matter", J. Neuroscience 1999 19(22):9986-9995.
Ramalho-Santos et al., "Stemness":Transcriptional Profiling of Embryonic and Adult Stem Cells, Science 2002 298:597-600.
Sette et al., "The role of stem cell factor and of alternative *c-kit* gene products in the establishment, maintenance and function of germ cells", Int. J. Dev. Biol. 2000 44:599-608.
Trempus et al., "Enrichment for Living Murine Keratinocytes from the Hair Follicle Bulge with the Cell Surface Marker CD34", J Invest Dermatol 2003 120:501-511.
Yuan et al., "Expression of the Green Fluorescent Protein in the Oligodendrocyte Lineage:A Transgenic Mouse for Developmental and Physiological Studies", J. Neuroscience Research 2002 70:529-545.

* cited by examiner

*Primary Examiner*—Thaian N Ton
(74) *Attorney, Agent, or Firm*—Licata & Tyrrell P.C.

(57) ABSTRACT

The present invention relates to methods for isolating infrequently-dividing, slow-cycling cells, a feature which is typical of stem cells in their niche. The methods of the present invention are advantageously used as classical stem cells can be isolated. Further provided are methods for generating clonal populations and inhibiting the differentiation of these cells. In addition markers for distinguishing these cells from progenitor cells are also disclosed.

1 Claim, No Drawings

METHOD FOR ISOLATING A SELF-RENEWING, MULTIPOTENT, SLOW-CYCLING CELL

This application claims priority to U.S. Patent Application No. 60/524,466 filed Nov. 24, 2003, U.S. Patent Application No. 60/604,450 filed Aug. 25, 2004, and is the national stage entry of PCT/US04/37925 filed Nov. 12, 2004, all of which are incorporated by reference in their entirety.

This invention was supported in part by funds from the U.S. government (NIH Grant Nos. AR 050452 and AR 31727) and the U.S. government has certain rights in the invention.

BACKGROUND OF THE INVENTION

Stem cells are slow-cycling, undifferentiated, or immature cells that are capable of giving rise to specialized cell types and ultimately to differentiated cells. These differentiated cells comprise the fully functional organs and tissues within the adult animal and are the end-product of embryonic development. Stem cells have two main characteristics. First, unlike any other cells, they are capable of replenishing tissues by generating, dividing and differentiating. Often, stem cells are multipotent, able to give rise to more than one type of mature cell/tissue. Second, stem cells are also able to renew themselves so that an essentially endless supply of mature cell types can be generated when needed. Because of this capacity for self-renewal, stem cells are therapeutically useful for the regeneration and repair of tissues.

The potency of a stem cell is measured by the variety of different cell types it can ultimately produce. The most potent stem cell is the pluripotent stem cell which can give rise to all cell types of the body (Wagner (1990) *EMBO J.* 9:3025-3032; Matsui et al. (1992) *Cell* 70:841-847; Resnick et al. (1992) *Nature* 359:550-551). Other stem cells exist and include multipotent stem cells which give rise to two or more different cell types. For example, the multipotent hematopoietic stem cell is capable of giving rise to all cell types of the blood system (Jones et al. (1990) *Nature* 347:188-189; Fleming et al. (1993) *J. Cell Biol.* 122:897-902). Other known multipotent stem cells include a neuronal stem cell, a neural crest stem cell (Reynolds and Weiss (1992) *Science* 255:1707-1710; Stemple and Anderson (1992) *Cell* 71:973-985), and a hair follicle stem cell (Taylor et al. (2000) *Cell* 102:451). Bipotential stem cells are also considered multipotent stem cells since they give rise to more than one cell type. Specific examples of bipotential stem cells include the O-2A progenitor (Lillien and Raff (1990) *Neuron* 5:111-119; McKay (1989) *Cell* 58:815-821; Wolswijk and Noble (1989) *Development* 105:387-400) and the sympathoadrenal stem cell (Patterson (1990) *Cell* 62:1035-1038). An example of a monopotent stem cell is the stem cell that resides in the epidermis (Jones and Watt (1993) *Cell* 73:713-723).

The usefulness of stem cells for tissue regeneration and repair has been shown in several systems. For example, grafting of a hematopoietic stem cell has been shown to rescue an animal which has had its bone marrow subjected to lethal doses of radiation (Jones et al. (1990) supra). An O-2A progenitor has also been shown to remyelinate spinal cord neurons that have been chemically demyelinated (Groves et al. (1993) *Nature* 362:453-455). Further, epidermal stem cells have been used for grafting skin in burn patients (Green (1980) *Scientific American*).

Thus, differentiated stem cells with a desired potency and lineage specificity provides an unlimited supply of source material for tissue regeneration and repair and the treatment of a broad range of diseases.

To obtain specific cell lineages differentiated from the pluripotent stem cell, in vivo mechanisms to direct the differentiation into specific cell lineages have been used. For example, stem cells of a neuronal lineage have been isolated after modifying pluripotent stem cells with a reporter construct and then reintroducing them into an early stage embryo (Ott et at. (1994) *J. Cell. Biochem. Supplement* 18A:187). The reporter construct is expressed during neurogenesis and cells expressing the reporter gene are dissected out and placed in culture. Through in vivo mechanisms, this method allows for the isolation of cells committed to the neuronal lineage but, again, the dissected cells once placed in culture proceed to terminal differentiation.

U.S. Pat. No. 5,639,618 teaches a method of isolating a lineage-specific stem cell in vitro, by transfecting a pluripotent embryonic stem cell with a construct containing a regulatory region of a lineage-specific gene operably linked to a DNA encoding a reporter protein; culturing the pluripotent embryonic stem cell under conditions such that the pluripotent embryonic stem cell differentiates into a lineage-specific stem cell; and separating the cells which express the reporter protein from the other cells in the culture, wherein the cell which expresses the reporter protein is an isolated lineage-specific stem cell.

The most common system for stem cell identification involves the use of proteins expressed on the surface of cells as markers to identify cell types. Using fluorescently-tagged antibodies that bind to these surface proteins, cells expressing the appropriate proteins can be separated using fluorescent activated cell sorting (FACS) analysis. For example, Trempus, et al. ((April 2003) *J. Invest. Dermatol.* 120(4):501-11) teach the isolation of live CD34+ keratinocytes using antibodies to CD34 and alpha 6 integrin in combination with fluorescent-activated cell sorting. However, the identification and purification of stem cells using this type of method can be variable and difficult due to a lack of knowledge regarding the correlation between surface marker expression and stem cell specificity and further due to variations in antibody binding efficiencies (Alison et al. (2002) *J. Pathol.* 197:419-423). Although many characteristics of hematopoietic stem cells have been identified, the properties of most stem cells remain poorly defined, precluding the ability to identify markers common to all stem cells. Similarly, common markers distinguishing multipotent and pluripotent stem cells have not been heretofore defined (Jackson et al. (2002) *J. Cell. Biochem. Suppl.* 38:1-6). Thus, there is a need in the art for methods of identifying and isolating slow-cycling cells such as stem cells. The present invention addresses this long-felt need.

SUMMARY OF THE INVENTION

The present invention relates to a method for isolating a self-renewing, multipotent, slow-cycling cell based on the presence and expression level of surface markers. The method involves obtaining a population of cells from a sample and sorting the population of cells based on the presence of CD34 and the amount of a selected slow-cycling cell marker expressed by each cell, so that a self-renewing, multipotent, slow-cycling cell is isolated.

The present invention further relates to a method for isolating and purifying a slow-cycling cell via the retention of a reporter protein. The method involves introducing into a cell or tissue a nucleic acid sequence encoding a regulatable transcription factor operably linked to a promoter that is active in, but not exclusive to, the slow-cycling cell of interest and further introducing into said cell a nucleic acid sequence encoding a long-lived, preferably fluorescently labeled, reporter protein operably linked to a regulated promoter to which the regulatable transcription factor binds. The regulatable transcription factor is first activated, thereby increasing the expression and accumulation of the reporter and subsequently inactivated so that expression of the reporter is decreased or inhibited. After a sufficient amount of time to allow for multiple cell cycles, the rapidly dividing and differentiating cells dilute and lose the long-lived, fluorescent reporter protein. Consequently, the slow-cycling cells are the only cells that retain the reporter protein over time. These slow-cycling cells can be detected and sorted by, for example, FACS analysis of single cell suspensions. A slow-cycling cell is one which has a high level of reporter protein present. In particular embodiments, the slow-cycling cells expressing a high level of reporter protein are further sorted based on the presence of CD34 and the amount of a selected slow-cycling cell marker. A non-human transgenic animal model for use in accordance with the method of the invention is further provided.

The present invention also provides methods for maintaining and generating a clonal population of selected self-renewing, multipotent cells. A clonal population of self-renewing, multipotent cells is generated by incubating a selected, isolated, self-renewing, multipotent, slow-cycling cell in the presence of about 0.2 mM to 0.5 mM calcium and a layer of fibroblast cells. A method for inhibiting the growth of a selected cell is also provided by contacting a selected cell with an effective amount of BMP6 or FGF-18 thereby inhibiting the growth of the cell. Cells isolated and maintained in accordance with these methods are desirable as they will differentiate into various lineages, for example, epidermal, neuronal, or glial cells.

DETAILED DESCRIPTION OF THE INVENTION

Isolation of human embryonic stem cells is a sensitive issue and therefore alternative and readily available sources of stem cells are of particular interest in tissue regeneration and repair, the treatment of a broad range of diseases, and basic research to understand the properties of adult stem cells and their ability to divide and differentiate along different lineages.

Skin is an attractive system for exploring the molecular and biological features of adult stem cells and their lineages. Its epithelium is large and accessible, and both epidermis and its appendages undergo continuous renewal and maintain reservoirs of multipotent epithelial stem cells whose descendants are highly organized both spatially and temporally. Epidermis maintains homeostasis by proliferation of a single (basal) layer of mitotically active cells that contain both transiently amplifying and stem cells (Fuchs and Raghavan (2002) *Nat. Rev. Genet.* 3:199; Potten (1974) *Cell Tissue Kinet.* 7:77; Potten and Morris (1988) *J. Cell Sci. Suppl.* 10:45; Mackenzie (1997) *J. Invest. Dermatol.* 109:377). Transiently amplifying cells withdraw from the cell cycle, detach from an underlying basement membrane and terminally differentiate as they move towards and are sloughed from the skin surface (Fuchs and Raghavan (2002) supra).

Contiguous with the epidermal basal layer is the outer root sheath of the hair follicle. The basal layer and outer root sheath share a large number of biochemical properties. In the follicle bulb, rapidly proliferating, relatively undifferentiated matrix cells terminally differentiate in upward concentric rings to form the inner root sheath and hair shaft. Epithelial-mesenchymal interactions between the matrix and the dermal papilla are necessary to maintain matrix character (Jahoda et al. (1984) *Nature* 311:560). The dermal papilla also functions to activate epithelial stem cells during hair-cycling, as the lower follicle undergoes (initially synchronous) cycles of growth (anagen), destruction (catagen) and rest (telogen). The niche for these stem cells is thought to be the bulge at the base of the non-cycling follicle segment. Following the rest period (telogen), induction of a new anagen involves a dermal papilla stimulus to recruit one or more stem cells to regenerate the lower follicle.

When skin of a 3 to 6 day-old mouse is uniformly labeled with $^3$H-thymidine and chased for 4 to 8 weeks, the bulge is marked as the residence of >95% of the label-retaining cells, i.e., infrequently cycling cells (Cotsarelis et al. (1990) *Cell* 61:1329; Morris and Potten (1999) *J. Invest. Dermatol.* 112:470; Taylor et al. (2000) supra). When the skin is then pulsed with BrdU, double-labeled cells, presumably originating from the bulge, are found elsewhere within the follicle (Taylor et al. (2000) supra). In wounded skin, rapidly dividing transiently amplifying cells from the upper outer root sheath (infundibulum) migrate to the basal epidermal layer within 24 hours to replenish the damaged epidermis (Taylor et al. (2000) supra). In addition, when dissected whisker bulges of lacZ-expressing rats are combined with dermal papilla and then transplanted, lacZ progeny can be detected in the resulting epidermis, hair follicles and sebaceous glands (Oshima et al. (2000) *Cell* 104:233; Kobayashi et al. (1993) *Proc. Natl. Acad. Sci. USA* 90:7391; Rochat et al. (1994) *Cell* 76:1063). Moreover, when rat whisker follicles are dissected and cultured, keratinocytes from segments harboring the bulge yield the largest colonies (Oshima et al. (2000) supra; Kobayashi et al. (1993) supra; Rochat et al. (1994) supra).

The present invention now provides methods for isolating adult stem cells (e.g., skin epithelial stem cells). Adult stem cells are isolated based upon the principle that stem cells are typically the only cells which are both slow-cycling and for which a tissue-specific promoter (e.g., a keratinocyte-specific promoter) is active. By way of illustration, bulge label-retaining cells were purified and characterized. The transcriptional profile of these stem cells was determined and compared with closely related progeny cells in the basal epidermal layer and upper outer root sheath, above the bulge. These studies uncovered more than 100 new genes which were preferentially up-regulated in the slow-cycling cells residing within the stem cell niche.

As used herein, the general use of the terms a quiescent or slow-cycling cell, unless specifically defined, is intended to include a stem cell (such as a pluripotent, multipotent, bipotential, and monopotent cell) which is an unspecialized cell that is capable of replication or self-renewal, and can develop into specialized cells of a variety of cell types or lineages. More commonly, a stem cell is a cell that, upon division, produces dissimilar daughters, one replacing the original stem cell, the other differentiating further. Other slow-cycling cells include, for example, closely-related progeny of stem cells (e.g., suprabasal cells of the epidermal bulge).

Slow-cycling stem cells can be recombinantly-tagged to facilitate isolation. By way of illustration, transgenic mice were engineered to express a stable histone H2B-GFP transgene (Kanda et al. (1998) *Curr. Biol.* 8:377) under the control of a regulatory element responsive to tetracycline-mediated repression (TRE). Subsequently, 20 of the most tightly regulated of TRE-mCMV-H2BGFP transgenic mice were identified and bred to mice harboring a K5-tetVP16 transgene (Diamond et al. (2000) *J. Invest. Dermatol.* 115:88) to restrict tet-controlled induction and repression to skin epithelium.

To validate the efficacy of the tet$^{off}$ H2B-GFP system, doxycycline (Tet) was first added to the diet of pregnant, double-transgenic mothers and their offspring. Under these conditions, TRE-mCMV-H2B-GFP was faithfully and quantitatively suppressed until 2 weeks after Tet was withdrawn. In contrast, mice never exposed to Tet exhibited high levels (~$5\times10^3$ units above background) of GFP-fluorescence throughout the skin epithelium, in agreement with the activity of K5/K14 promoters in stem cells (Diamond et al. (2000) supra; Vasioukhin et al. (1999) *Proc. Natl. Acad. Sci. USA* 96:8551). This was consistent with the high stability of H2B-GFP and with K5 promoter activity. When mice were fed Tet beginning at 4 weeks postnatally, overall GFP declined over 3-4 weeks until only a small percent of backskin cells retained fluorescence at $\geqq10^3$ units above background and these resided exclusively in the bulge. Infrequent GFP-intermediate cells (~$10^2$ above background) were in the epidermis, and longer exposure revealed their location in patches (Mackenzie (1997) supra). If these represent basal layer stem cells, they divide more frequently than bulge label-retaining cells.

Fluorescence microscopy analyses of skin sections revealed an average of 40-120 cells retaining 10-200× higher H2B-GFP than other skin epithelial cells (see also Braun et al. (2003) *Development* 130:5241). Unexpectedly, the brightest label-retaining cells were frequently clustered on one side of the follicle. Taken together, this method solves a major problem of fluorescently marking slow-cycling stem cells in a cell type-specific manner in the absence of known specific cell surface markers. While keratinocyte-specific Tet$^{off}$VP16 mice were used for these studies, it is contemplated that a TRE-CMV-H2BGFP animal could be used and mated with any comparable animal expressing other promoter/enhancer driven, regulatable activators/repressors.

Previous nucleotide pulse and chase experiments have demonstrated that bulge label-retaining cells contribute to forming the new follicle during cycling (Taylor et al. (2000) supra). H2B-GFP label-retaining cells afforded a more sensitive method to track label-retaining cell fate, as well as a direct method to monitor simultaneous changes in divisions and biochemistry within label-retaining cells as they are activated. To monitor label-retaining cell participation in follicle formation, 4 week-old mice were switched to a Tet diet (chase). After a 4 week chase, the majority of dorsal torso follicles were still in their second telogen and label-retaining cells were restricted to the bulge.

Cells positive for the proliferating nuclear antigen Ki67 were restricted to the sebaceous gland, infundibulum (upper outer root sheath) and epidermal basal layer. By 4.5 weeks of chase, many follicles had initiated a new anagen and formed the secondary hair germ. Most cells in the upper bulge remained GFP-bright and Ki67-negative, but occasional GFP-bright cells at the bulge base were Ki67-positive. The paucity of dividing cells within the bulge was substantiated by immunoreactivity for phosphorylated histone H3 (P-H3), which marks the G2/M phase of the cell cycle. Although cells in mitosis were rare, the ones in the vicinity of the bulge were always located at or below the juncture between bulge and hair germ. Thus, if divisions occur within the bulge, their low frequency made them difficult to detect. Antibodies against nuclear basonuclin, associated with keratinocyte proliferation (Tseng and Green (1994) *J. Cell. Biol.* 126:495), further delineated this transition zone between label-retaining cells and their immediate progeny. Anti-K19, previously identified as a bulge marker (Michel et al. (1996) *J. Cell Sci.* 109:1017), was also brightest just prior to this zone. As hair germs developed (early anagen II), label-retaining cell descendants below the zone were strongly Ki67-positive and H2B-GFP-dim, only visible upon overexposure. Collectively, these findings indicate that only a small subset of bulge H2B-GFP label-retaining cells exit the niche, and that soon after exit, they rapidly proliferate to initiate new follicle downgrowth, and change their biochemistry.

Follicle downgrowth and outer root sheath formation is complete by late anagen (9.5 weeks), an active period of inner root sheath and hair production (Muller-Rover et al. (2001) *J. Invest. Dermatol.* 117:3). At this stage, the brightest GFP-labeled cells, many with comparable intensity to the prior hair-cycle, were still clustered within the bulge. A trail of decreasingly GFP-bright cells were visible below the bulge along the most outer root sheath layer. Overexposure revealed a gradient until about half-way down the follicle. Only an occasional GFP-labeled cell was detectable in the lower outer root sheath even when overexposed. The gradient was comparably distributed on both sides of the outer root sheath, despite the asymmetry of label retention within the bulge.

Throughout the hair-cycle, Ki67 and H2B-GFP exhibited an inverse correlation. The data indicate that the late-anagen cells within the outer root sheath just below the bulge represent an unusual group of label-retaining cell progeny that have not undergone many divisions since exiting the bulge. The data seem most consistent with a top-down model for forming the outer root sheath, whereby label-retaining cell progeny divide only a few times prior to establishing residence in the outer root sheath below the bulge and withdrawing from the cell cycle, while outer root sheath cells further down divide more, and near the base, they retain proliferative status through late anagen. This data, however, does not rule out an alternative possibility whereby the late anagen, outer root sheath cells below the bulge represent recently generated label-retaining cell progeny which are not stationary, but rather migrating cells, which move along the outer root sheath and convert to rapidly proliferating matrix cells at the follicle base (Oshima et al. (2000) supra; Kobayashi et al. (1993) supra; Rochat et al. (1994) supra). Whether stationary or migrating, these unusual cells, which often express bulge markers, are close bulge descendants which are not rapidly proliferating.

To determine whether bulge label-retaining cells could respond directly to skin wounds, 8 week-old mice whose H2B-GFP expression had been suppressed for 4 weeks were wounded to selectively label the bulge. In response to either small penetrating skin wounds or surface scraping, GFP-bright cells were consistently detected outside the bulge within 24-48 hours post injury. Fluorescence was sometimes weaker than in label-retaining cells, indicative of proliferation. In some cases, fluorescence was comparable to the brightest label-retaining cells. These GFP-bright cells did not seem to be simply scattered bulge cells, since they localized to surrounding infundibulum. Additionally, anti-laminin 5 immunoreactivity often revealed an underlying basement membrane, indicative of a platform for their migration. Label-retaining cells outside the bulge exhibited immunoreactivity for nuclear anti-junk, a stress-response protein. Not seen in unwounded skin, such bright nuclear staining also occurred within activated cells of the infundibulum, epidermis and occasionally, bulge. These data are in agreement with previous studies suggesting that label-retaining cells contribute to the repopulation not only of the infundibulum but also the epidermis (Taylor et al. (2000) supra; Oshima et al. (2000) supra; Kobayashi et al. (1993) supra; Rochat et al. (1994) supra). In addition, these observations indicate that in response to a wound stimulus, H2B-GFP label-retaining cells change their biochemistry, exit the bulge, migrate and proliferate.

Immunofluorescence microscopy revealed that the zone harboring keratinocyte-specific, H2B-GFP label-retaining cells was more restricted than that defined with other known markers enriched for bulge cells. This included K15, integrins $\alpha$6 and $\beta$1 and CD34 (Jones et al. (1995) *Cell* 80:83; Lyle et al. (1999) *J. Investig. Dermatol. Symp. Proc.* 4:296; Tani et al. (2000) *Proc. Natl. Acad. Sci. USA* 97:10960; Merrill et al. (2001) *Genes Dev.* 15:1688; Trempus et al. (2003) *J. Invest. Dermatol.* 120:501). Therefore, the method of the invention affords a unique potential for isolating and characterizing stem cells residing exclusively within this niche. After defining appropriate conditions, single-cell suspensions from skins of 8 week-old transgenic mice (4 weeks chase) were subsequently subjected to fluorescence-activated cell sorting (FACS) analysis. Most cells were GFP-negative; 12% of the population displayed 10 to $10^4$-fold fluorescence above background; 1-2% exhibited $10^3$-$10^4$-fold fluorescence.

Populations gated at $10^3$-$10^4$-fold (GFP$^{high}$) and $10^2$-fold (GFP$^{low}$) excluded propidium iodide and exhibited surface expression of $\beta$4, $\beta$1 and $\alpha$6, typical of outer root sheath and basal layer epidermal cells. However, GFP$^{high}$ cells were enriched in the bulge cell-preferred marker CD34 (Ramalho-Santos et al. *Science* 298:597), while GFP$^{low}$ cells possessed more CD71, a marker downregulated by bulge cells (Tani et al. (2000) supra). Semi-quantitative fluorescence microscopy documented that GFP$^{high}$ cells shared comparable fluorescence intensity to those within the bulge, while GFP$^{low}$ fluorescence placed them outside the niche.

GFP$^{high}$ and GFP$^{low}$ cells expressed epidermal/outer root sheath keratins 5, 14 and 15 (Fuchs and Raghavan (2002) supra; Lyle et al. (1999) supra), but not the differentiation marker K1 (Fuchs and Raghavan (2002) supra). As judged by cytospin-immunofluorescence analyses of four different markers (n=200-800 cells/marker), these populations were each >90% homogeneous. FACS sorting based on surface $\beta$4 expression also identified a near-homogeneous population of KS-positive cells but with significantly reduced fluorescence over GFP$^{low}$ cells. This was expected, since the $\beta$4-positive fraction encompassed the majority of the basal level epidermis and outer root sheath, whereas GFP$^{low}$ cells were only a subset of this population. Semi-quantitative reverse transcriptase PCR further characterized the nature of these populations.

Cell-cycle profiles revealed that only 0.5% of GFP$^{high}$ cells were in G2/M; in contrast, the other populations analyzed displayed six and 14-fold more cells in G2/M. Taken together, these data defined the GFP$^{high}$ cells as a homogenous group of quiescent stem cells (label-retaining cells) isolated directly from their niche. The two progeny populations represented primarily outer root sheath and basal layer epidermal cells, i.e., the progeny most closely similar to stem cells.

Microarray analyses revealed the transcriptional profiles of bulge stem cells and the two progeny populations ($10^5$ cells/sample, in duplicate; AFFYMETRIX MG-U74Av2 chips). AFFYMETRIX software (MAS5.0) was used to analyze raw image files collected from hybridizations, and high stringency analyses uncovered distinguishing features of these populations.

Approximately 4800 of 12,000 mRNAs were scored as present in each population. When compared with analogous AFFYMETRIX stem cell databases from hematopoietic, embryonic and neuronal tissues (Ramalho-Santos et al. (2002) *Science* 298:597; Ivanova et al. (2002) *Science* 298:601), only 372 (8%) transcripts scored as specific for bulge label-retaining cells. This mRNA pool was enriched for keratinocyte markers. In contrast, 68% of bulge label-retaining cell mRNAs were shared with the other stem cells. Although many of those encoded housekeeping proteins, ~40% of the mRNAs specifically upregulated in skin label-retaining cells vs. their closely related progeny were also shared among other stem cells (~60 of 154 total mRNAs).

Some label-retaining cell mRNAs, including $\beta$1, $\alpha$6, Tcf3 and CD34, encoded known bulge-preferred markers also present in some other stem cells (Jones et al. (1995) supra; Lyle et al. (1999) supra; Tani et al. (2000) supra; Merrill et al. (2001) supra; Trempus et al. (2003) supra). Other label-retaining cell transcripts had only been observed in other stem cells and not skin. These included stem cell factor (kit ligand), Dab2, ephrin tyrosine kinase receptors (Ephs), tenascin C (Tnc), IL-11 receptor, Id binding protein 2 (Idb2), four-and-a-half lim domains (Fhl1), growth arrest specific (Gas) proteins and Bmi-1 (Sette et al. (2000) *Int. J. Dev. Biol.* 44:599; Garcion et al. (2001) *Development* 128:2485; Hocevar et al. (2003) *EMBO J.* 22:3084; Park et al. (2003) *Nature* 423:302; Lessard and Sauvageau (2003) *Nature* 423:255). Many of these mRNAs were up-regulated by 2- to 10-fold in skin label-retaining cells relative to their close progeny. Table 1 summarizes the results of these experiments.

TABLE 1

| Category | mRNAs (Fold Induction) |
|---|---|
| Present in hematopoietic, embryonic and neuronal stem cells | Stem cell factor (kit-1)(2x)*, Bcl2(2x), S100 A6(3x), ACF7(3x), EfnB2(2x)*, $\beta$1-integrin(P), Bmi-1(P), $\alpha$6-integrin(P), Lgals1(3x), thioredoxin(3x)*, Mfhas1(2x), Fst1(6x)*, Ctbp2(2x)*, Ndr2(3x)*, Ppap2a(8x), Ndn(3x), Gcat(3x)*, Ak1(3x)*, actinin $\alpha$1(4x), Fln$\beta$(3x), Fhl1(3x)*, Eps8(4x)*, Peg3(7x), Fts(2x), Rcn2(2x)*, Idb1(2x), Idb2(8x), Myolb(4x), Pbx3(4x), syndecan bp(2x), hist1h2bc(3x), Ptprk(3x)* |
| Present in embryonic and neuronal stem cells | Dab2(9x), Enah(2x), Fzd2(5x), Tnc(3x), profiling(3x), Bdnf(8x), Idb4(4x), GasI(4x), Homer2(3x), Sparc(2x) |
| Present in embryonic stem cells | Osf(5x), Ctgf(8x), Ltbp1(8x) |
| Present in hematopoietic stem cells | CD34(9x)*, eya2(3x)*, Vdr(2x)*, IL-11ra2(3x)*, NFATc1(2x), Mad4(2x)*, EfnB1(2x)*, Tcf3(3x)* |
| Called absent in hematopoietic, embryonic and neuronal stem cells | Dkk3(5x), Sfrp1(7x), EfnA4(2x), Barx2(2x), Fbln1(3x), Tekt2(14x), Odz2(3x), Sema3c(4x), Mitf(5x), Col6a1(3x), Tcfap2b(3x) |

Presence (P) or fold-increase are in parentheses.

Published stem cell databases (Ramalho-Santos et al. (2002) supra) and lists (Ivanova et al. (2002) supra) were also used in the analyses.

*Denotes mRNAs increased in hematopoietic stem cells relative to terminally-differentiated progeny (Ivanova et al. (2002) supra).

Although complete verification was beyond the scope of this study, many mRNAs were validated by semi-quantitative PCR and when possible, by immunofluorescence with monospecific antibodies.

Factors more specific to the label-retaining cells relative to the other stem cell databases may simply be reflective of the status of the skin stem cell niche at a given time. Unexpectedly, only a small fraction of genes seem to be used selectively by skin label-retaining cells to deal with their special skin environment. By comparing skin stem cells against closely-related, relatively undifferentiated progeny, a specific subset of genes were identified that overlapped with the other stem cells databases, previously compared against either whole tissue/organ or differentiated cells (Ramalho-Santos et al. (2002) supra; Ivanova et al. (2002) supra). This subset of putative stem cell factors is likely involved in stem cell maintenance and/or activation. Such factors include those involved in regulating cell growth and survival, those able to sense and respond to growth factors, hormones and extracellular matrix, and those able to remodel transcriptional status. Together, these findings provide new insights into the relation between bulge label-retaining cells and other stem cell populations.

A novel and broadly applicable method of fluorescently-labeling slow-cycling cells in a cell type-specific fashion has now been demonstrated. As exemplified herein, this method was used to purify and characterize slow-cycling skin cells and mark the stem cell niche. The movements and interactions of these slow-cycling cells with neighboring cells was monitored, and it was found that skin stem cells rarely divide within their niche, exit when stimulated, and change their properties upon exit. Further, the transcriptional profile of the isolated stem cells was determined and, when compared to closely-related progeny and other stem cells, defined unique features of the stem cell niche. Thus, one advantage of the method of the present invention is the ability to isolate and characterize not only stem cells (e.g., bulge label-retaining cells), but also a pool of closely-related progeny.

Accordingly, the present invention is a method for isolating a tissue-specific or lineage-specific, slow cycling cell involving the initial steps of introducing into a cell or tissue a nucleic acid sequence encoding a regulatable transcription factor operably linked to a promoter that is active in, but not necessarily exclusive to, the slow-cycling cells of interest and further introducing into said cell or tissue a nucleic acid sequence encoding, preferably, a fluorescent, long-lived, stable reporter which is operably linked to a regulated promoter to which the regulatable transcription factor binds so that expression of the reporter protein is tightly controlled. By first activating the regulatable transcription factor, the fluorescent, long-lived reporter protein accumulates in all cells where the promoter of the transcription factor is active. By subsequently inactivating the regulatable transcription factor, expression of the reporter protein is decreased. As cells go through multiple cell cycles, the reporter protein amounts are diluted as the reporter protein is partitioned to daughter cells. Cells containing the highest levels of the reporter protein are indicative of said cells being the slow-cycling cell s of the population.

In accordance with this method of the invention, a promoter operably linked to the regulatable transcription factor is active (i.e., capable of producing a transcript) in, although not necessarily exclusive to, the slow-cycling cells of interest. In some circumstances, such as that disclosed herein for skin, the promoter can be a tissue-specific promoter. The regulatable transcription factor must be capable of binding the regulated promoter which is operably linked to nucleic acid sequences encoding the reporter. The ability of transcription factor to control reporter gene expression should be tightly regulated, as exemplified by the tetracycline regulatable transcription factor. As used herein, a promoter which is operably associated or operably linked to nucleic acid sequences encoding a regulatable transcription factor or reporter means that the sequences are joined and positioned in such a way as to permit transcription. Two or more sequences, such as a promoter and any other nucleic acid sequences are operably associated if transcription commencing in the promoter will produce an RNA transcript of the operably associated sequences of interest.

In general, a promoter encompasses nucleic acid sequences of a minimal promoter sequence which is not itself transcribed but which serves at least in part to position the transcriptional machinery for transcription. The minimal promoter sequence is linked to the transcribed sequence in a 5'-to-3' direction (i.e., the promoter is located upstream of the transcribed sequence) to form a contiguous nucleotide sequence. The activity of such a minimal promoter is dependent upon the binding of a specific transcriptional activator or repressor to one or more operatively-linked regulatory sequences or elements. An example of a minimal promoter is from the human cytomegalovirus (CMV; Boshart, et al. (1985) *Cell* 41:521-530). Preferably, nucleotide positions between about +75 to −53 and +75 to −31 are used. Other suitable minimal promoters are known in the art or may be identified by standard techniques. For example, a functional minimal promoter which activates transcription of a contiguously-linked reporter gene (e.g., chloramphenicol acetyl transferase, β-galactosidase or luciferase) may be identified by progressively deleting upstream sequences until the promoter no longer activates expression of the reporter gene alone but rather requires the presence of an additional regulatory sequence(s).

A promoter further encompasses at least one regulatory sequence or element located upstream of the minimal promoter sequence. A transcriptional activator or repressor typically binds to a regulatory sequence and controls expression of the nucleic acid sequence of interest in a temporal, spatial, tissue, or stimulus-specific manner. In a typical configuration, a regulatory sequence(s) is operatively-linked upstream (i.e., 5') of the minimal promoter sequence at a suitable distance to stimulate or inhibit transcription of the target nucleotide sequence upon binding of a regulatable transcription factor to the regulatory sequence. That is, the transcription unit is comprised of, in a 5'-to-3' direction: a regulatory sequence(s) →a minimal promoter→a transcribed nucleotide sequence. It will be appreciated by those skilled in the art that there is some flexibility in the permissible distance between the regulatory sequence(s) and the minimal promoter, although typically the regulatory sequences will be located within about 200-400 base pairs upstream of the minimal promoter.

Promoters for use in the method of the invention may be one contiguous sequence isolated from a single gene or may be a fusion of promoters from two sources. For example, a regulated promoter may contain a minimal promoter from one source (e.g., CMV) and a regulatory sequence from another source (e.g., tet-responsive element).

A tissue-specific or lineage-specific promoter is one which controls expression of a regulatable transcription factor in a tissue-specific or lineage-specific manner, i.e., expression of the regulatable transcription factor is limited to specific tissue or lineage cell type. Examples of promoters which may be used include, but are not limited to, the albumin promoter (liver-specific; Pinkert, et al. (1987) *Genes Dev.* 1:268-277), lymphoid-specific promoters (Calame and Eaton (1988) *Adv. Immunol.* 43:235-275), promoters of T cell receptors (Winoto and Baltimore (1989) *ERMO J.* 8:729-733) and immunoglobulins (Banerji, et al. (1983) *Cell* 33:729-740; Queen and Baltimore (1983) *Cell* 33:741-748), neuronal-specific promoters (e.g., the neurofilament promoter; Byrne and Ruddle (1989) *Proc. Natl. Acad. Sci USA* 86:5473-5477), pancreas-specific promoters (Edlund, et al. (1985) *Science* 230:912-916), mammary gland-specific promoters (e.g., milk whey promoter; U.S. Pat. No. 4,873,316; EP 264,166), and regulatory regions from genes such as Dlx (Porteus et al. (1991) *Neuron* 7:221-229), Nlx (Price et al. (1991) *Nature* 351:748-751), Emx (Simeone et al. (1992) *EMBO J.* 11:2541-2550), Wnt (Roelink and Nuse (1991) *Genes Dev.* 5:381-388), En (McMahon et al. (1992) *Cell* 69:581-595), Hox (Chisaka and Capecchi (1991) *Nature* 350:473-479; Lufkin et al. (1991) *Cell* 66:1105-1119), acetylcholine receptor beta-chain (Otl et al. (1994) *J. Cell. Biochem. Supplement* 18A:177), Otx (Simeone et al. (1992) *Nature* 358:687-690; Otl et al. (1994) supra) and the like.

A regulatable transcription factor (i.e., transcriptional activator or repressor) for controlling expression of a regulated promoter is preferably a protein whose activity or ability to bind to a regulatory element is dependent on the administration of an exogenous molecule. Preferably, the regulatory protein tightly regulates expression of a nucleic acid sequence of interest (e.g., a reporter) which is operably linked to the regulated promoter. Tight regulation means that basal expression of the nucleic acid sequence of interest is very low and is inducible to high levels. Induction can be a positive effect (adding rather than removing an exogenous molecule), and should have limited pleiotropic effects in mammalian cells. Further, a regulatory protein(s) should also have no effects on endogenous gene expression, and ideally be encoded by nucleic acid sequences isolated from the host cell to minimize potential immunogenicity.

Exemplary regulatable transcription factors and their cognate promoter regulatory sequences or elements include, but are not limited to, those regulated by the antibiotic tetracycline (Tet) (Gossen and Bujard (1992) *Proc. Natl. Acad. Sci. USA* 89:5547-5551; Gossen et al. (1995) *Science* 268:1766-1769); the insect steroid ecdysone or its analogs (No et al. (1996) *Proc. Natl. Acad. Sci. USA* 93:3346-3351); the antiprogestin mifepristone (RU486) (Wang et al. (1994) *Proc. Natl. Acad. Sci. USA* 91:8180-8184); and chemical 'dimerizers' such as the immunosuppressant rapamycin and its analogs (Rivera et al. (1996) *Nature Med.* 2:1028-1032; Ho et al. (1996) *Nature* 382:822-826; Amara et al. (1997) *Proc. Natl. Acad. Sci. USA* 94:10618-10723; Magari et al. (1997) *J. Clin. Invest.* 100:2865-2872). Such regulatory systems involve the drug-dependent recruitment of a transcriptional activation domain to a promoter driving expression of a nucleic acid sequence of interest, but differ in the mechanism of recruitment (for a review see Clackson (1997) *Curr. Opin. Chem. Biol.* 1:210-218).

In general, the Tet-regulatory protein encompasses the natural Tet-controlled DNA binding domain (DBD) of the *E. coli* Tet repressor (TetR) fused to a heterologous transcriptional activation domain (AD), usually herpes virus VP16. Transcription of nucleic acid sequences operably linked with a minimal promoter and upstream TetR binding sequences (i.e., tetracycline-responsive promoter element which is composed of concatemers of the Tet operator) can then be controlled by Tet, or analogs thereof such as doxycycline. In the Tet-off system (Gossen and Bujard (1992) supra), the Tet-regulatory protein binds to the tetracycline-responsive promoter element and activates transcription of the target nucleic acid sequence in the absence of tetracycline or doxycycline. In the Tet-on system (Gossen et al. (1995) supra), the regulatory protein is a reverse tetracycline-controlled transactivator which contains a four amino acid change in the tetR DNA binding moiety thereby altering the binding characteristics of the regulatory protein such that it can only recognize the tet operator sequences in the tetracycline-responsive promoter element in the presence of the tetracycline or doxycycline.

Similar principles underlie the ecdysone (Ec) system, in which the natural Ec-dependent DBD from the Drosophila Ec receptor is coupled to VP16; the protein is co-expressed with another steroid receptor (RXR) to obtain Ec-activated transcription (No et al. (1996) supra). In the mifepristone system, drug-regulated transcription is achieved by fusing heterologous DBD (yeast GAL4) and AD (VP16) proteins to a mutant human progesterone receptor that is unaffected by endogenous hormones but is activated by synthetic antiprogestins (Wang et al. (1994) supra). While these former systems rely on allosteric control, dimerizer controlled transcription uses the principle of induced proximity (Clackson (1997) supra; Spencer (1996) *Trends Genet.* 12:181-187). In the dimerizer system, heterologous DBDs and ADs are each fused to a drug-binding domain, rendering transcription dependent on a bivalent drug that can crosslink the two proteins and reconstitute an active transcription factor. Homodimeric drugs can be used (Ho et al. (1996) supra; Amara et al. (1997) supra), however, a heterodimerizer such as rapamycin (Rivera et al. (1996) supra), which binds to the human proteins FKBP and FRAP, can also be used. In this case, a human chimeric DBD called ZFHD112 is joined to FKBP and the human NF-κB p65 AD is fused to FRAP. Addition of rapamycin dimerizes the two fusion proteins and activates transcription of genes downstream of ZFHD1 binding sites. Because rapamycin itself is immunosuppressive, nonimmunosuppressive analogs ('rapalogs') can be used in conjunction with a FRAP domain which has mutation(s) that accommodate modified drugs (Liberles et al. (1997) *Proc. Natl. Acad. Sci. USA* 94:7825-7830). It is contemplated that nucleic acid sequences encoding the two components of the transcription factor of the dimerizer system can be introduced consecutively or concurrently into the host cell on separate expression vectors or on the same vector (Pollock et al. (2000) *Proc. Natl. Acad. Sci. USA* 97(24):13221-6).

For the detection and isolation of a tissue-specific, slow-cycling cell, the regulated promoter is operably linked to a nucleic acid sequence encoding a reporter. A reporter refers to any sequence that is detectable and distinguishable from other sequences present in host cells. Preferably, the reporter nucleic acid sequence encodes a long-lived, stable protein (e.g., protease resistant or remains in a cell through multiple cell cycles) that is readily detectable either by its presence, or by its activity that results in the generation of a detectable signal. A nucleic acid sequence encoding the reporter is used in the invention to identify and isolate a tissue-specific, slow-cycling cell. In cases where the reporter is not inherently long-lived, the reporter can be fused with another protein which increases it stability in the cell. Suitable fusions for enhancing the stability of a reporter can include, but not be limited to, a histone 2B-reporter fusion (Kanda et al. (1998) *Curr. Biol.* 8:377) or an affibody immunoconjugate (Ronnmark, et al. (2003) *J. Immunol. Methods* 281(1-2):149-60).

It is contemplated that a variety of enzymes can be used as reporters as long as they are modified to be long-lived. Such reporters include, but are not limited to, β-galactosidase (Nolan, et al. (1988) *Proc. Natl. Acad. Sci. USA* 85:2603-2607), chloramphenicol acetyltransferase (CAT; Gorman, et al. (1982) *Mol. Cell Biol.* 2:1044; Prost, et al. (1986) *Gene* 45:107-111), β-lactamase, β-glucuronidase and alkaline phosphatase (Berger, et al. (1988) *Gene* 66:1-10; Cullen, et al. (1992) *Meth. Enzymol.* 216:362-368). Transcription of the nucleic acid sequences encoding a reporter leads to production of the enzyme in host cells. The amount of enzyme present can be measured via its enzymatic action on a substrate resulting in the formation of a detectable reaction product. The method of the invention provides means for determining the amount of reaction product, wherein the amount of reaction product generated or the remaining amount of substrate is related to the amount of enzyme activity. For some enzymes, such as β-galactosidase, β-glucuronidase and β-lactamase, well-known fluorogenic substrates are available that allow the enzyme to convert such substrates into detectable fluorescent products.

A variety of bioluminescent, chemiluminescent and fluorescent proteins may be more preferable as light-emitting reporters because they can also be coupled to FACS analysis to facilitate the isolation of slow-cycling cells. Exemplary light-emitting reporters, which are enzymes and require cofactor(s) to emit light, include, but are not limited to, the bacterial luciferase (luxAB gene product) of Vibrio harveyi (Karp (1989) *Biochim. Biophys. Acta* 1007:84-90; Stewart, et al. (1992) *J. Gen. Microbiol.* 138:1289-1300), and the luciferase from firefly, Photinus pyralis (De Wet, et al. (1987) *Mol. Cell. Biol.* 7:725-737). In the case of these reporter proteins, it may be preferable to generate fusion proteins to enhance the stability of the reporter protein.

In particular embodiments, a reporter for use in accordance with the method of the invention is a light-emitting reporter, which does not require substrates or cofactors and includes, but is not limited to, the wild-type green fluorescent protein (GFP) of Victoria aequoria (Chalfie, et al. (1994) *Science* 263:802-805), modified GFPs (Heim, et al. (1995) *Nature* 373:663-4; WO 96/23810), and the gene products encoded by the Photorhabdus luminescens lux operon (luxABCDE) (Francis, et al. (2000) *Infect. Immun.* 68(6):3594-600). For such reporters, fusion of the reporter protein to highly stable proteins such as histone 2B or affibody conjugate may be desirable. Histone would be ideal because it is packaged into chromatin in non-cycling cells and hence very stable over time. Transcription and translation of the resulting long-lived, stable reporters leads to the accumulation of the fluorescent or bioluminescent proteins in test cells, which can be measured by a device, such as a fluorimeter, flow cytometer, or luminometer. Methods for performing assays on fluorescent materials are well-known in the art (e.g., Lackowicz (1983) In: Principles of Fluorescence Spectroscopy, New York, Plenum Press).

The host cells which contain the nucleic acid sequences encoding the reporter and which express products of the nucleic acid sequences encoding the reporter can be identified by at least four general approaches; detecting DNA-DNA or DNA-RNA hybridization; observing the presence or absence of marker gene functions (e.g., resistance to antibiotics); assessing the level of transcription as measured by the expression of reporter mRNA transcripts in the host cell; and detecting the reporter gene product as measured by immunoassay or by its biological activity.

Nucleic acid sequences for use in accordance with the method of the invention (i.e., nucleic acid sequences encoding a regulatable transcription factor operably linked to a promoter active in, but not necessarily exclusive to, the slow-cycling cells of interest and nucleic acid sequences encoding a reporter operably linked to a regulated promoter) can be introduced into a host cell as naked DNA or using well-known expression vectors. An expression vector can be a plasmid. Alternatively, an expression vector can be a virus, or a portion thereof, which allows for expression of a nucleic acid introduced into the viral vector. For example, replication-defective retroviruses, adenoviruses and adeno-associated viruses can be used. Protocols for producing recombinant retroviruses and for infecting cells in vitro or in vivo with such viruses can be found in Current Protocols in Molecular Biology, Ausubel et al. (eds.) Greene Publishing Associates, (1989), Sections 9.10-9.14 and other standard laboratory manuals. Examples of suitable retroviruses include pLJ, pZIP, pWE and pEM which are well-known to those skilled in the art. Examples of suitable packaging virus lines include ψCrip, ψCre, ψ2 and ψAm. The genome of adenovirus can be manipulated such that it encodes and expresses a nucleic acid sequence of the invention but is inactivated in terms of its ability to replicate in a normal lytic viral life cycle (Berkner, et al. (1988) *BioTechniques* 6:616; Rosenfeld, et al. (1991) *Science* 252:431-434; Rosenfeld, et al. (1992) *Cell* 68:143-155). Suitable adenoviral vectors derived from the adenovirus strain Ad type 5 dl324 or other strains of adenovirus (e.g., Ad2, Ad3, Ad7 etc.) are well-known to those skilled in the art. In vivo use of adenoviral vectors is described in Flotte, et al. ((1993) *Proc. Natl. Acad. Sci. USA* 90:10613-10617) and Kaplitt, et al. ((1994) *Nature Genet.* 8:148-153). Other viral vectors, such as those based on togaviruses, alpha viruses, or vaccinia virus can also be used. Alternatively, an adeno-associated virus vector such as that disclosed by Xu, et al. ((2001) *Gene Ther.* 8(17):1323-32) can be used to express a nucleic acid sequence of the invention.

While the nucleic acid sequences of the invention can be stably expressed or integrated into the genome of the host cell, the nucleic acid sequences can optionally be contained in a suicide vector capable of a longer existence than an isolated DNA molecule but not capable of permanent retention in the host cell. Such a vector can transiently express the nucleic acid sequences for a sufficient time to screen for or select a cell bearing the vector (e.g., cells expressing the reporter), but is then degraded or otherwise rendered incapable of expressing the nucleic acid sequences. Such a vector can be rendered suicidal by incorporation of a defective origin of replication (e.g., a temperature-sensitive origin of replication) or by omission of an origin of replication. Unlike gene therapy approaches where the goal is long-term vector maintenance and expression of the gene of interest, a vector for use in accordance with the present invention can be unstable and desirably lost from the host cell once it has been isolated as a slow-cycling cell. The use of an unstable vector is advantageous because, once isolate, the slow-cycling cell would no longer contain the recombinant vector. An expression vector can be introduced into a host cell by standard techniques for transforming cells. Transformation or transfection are intended to encompass all conventional techniques for introducing nucleic acid into host cells, including calcium phosphate co-precipitation, DEAE-dextran-mediated transfection, lipofection, electroporation, microinjection, polyethylene glycol-mediated transformation, viral infection, cell fusion, and ballistic bombardment. Suitable methods for transforming host cells may be found in Sambrook, et al. (Molecular Cloning: A Laboratory Manual, 2nd Edition, Cold Spring Harbor Laboratory press (1989)) and other laboratory manuals.

The number of host cells transformed with an expression vector will depend, at least in part, upon the type of expression vector used and the type of transformation technique used. Nucleic acids can be introduced into a host cell transiently, or for long-term regulation of gene expression, the nucleic acid is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is generally introduced into the host cells along with the nucleic acids of interest. Selectable markers for use herein include those which confer resistance to certain drugs, such as G418 and hygromycin. Selectable markers can be introduced on a separate plasmid from the nucleic acids of interest or introduced on the same plasmid. Host cells transfected with nucleic acids of the invention (e.g., a recombinant expression vector) and a gene for a selectable marker can be identified by selecting for cells using the selectable marker. For example, if the selectable marker encodes a gene conferring neomycin resistance, host cells which have taken up nucleic acid can be selected with G418 resistance. Cells that have incorporated the selectable marker gene will survive, while the other cells die.

In this method of the invention, expression of a reporter operably linked to a regulated promoter is controlled by a transcription regulatory protein. Thus, the regulatory protein and the target regulated promoter/reporter fusion should both be present in a host cell or organism. The presence of both the regulatory protein and the target regulated promoter/reporter in the same host cell or organism can be achieved in a number of different ways. The two components can be introduced into cells as two separate molecules (e.g., on two different expression vectors). In this case, a host cell is either co-transformed with the two vectors or successively transformed first with one expression vector and then the other expression vector. Alternatively, the nucleic acid sequences encoding the two components can be linked (i.e., colinear) in the same molecule (e.g., a single vector). In this case, a host cell is transformed with the single nucleic acid molecule.

The host cell can be a cell cultured in vitro or a cell present in vivo. The host cell can further be a fertilized oocyte, embryonic stem cell or any other embryonic cell used in the creation of non-human transgenic. A non-human transgenic animal model can be created, for example, by introducing a nucleic acid sequence of the invention into the male pronuclei of a fertilized oocyte, e.g., by microinjection, and allowing the oocyte to develop in a pseudopregnant female foster animal. Methods for generating transgenic animals, particularly animals such as mice, have become conventional in the art and are described, for example, in U.S. Pat. Nos. 4,736,866 and 4,870,009. Suitable mice strains which may be used in accordance with the method of the invention include, but are not limited to CD1 mice, BALB/c mice, and the like.

The generation of other species of non-human transgenic animals (e.g., rat, cow, pig, etc.) expressing a nucleic acid sequence disclosed herein is also contemplated using methods well-known in the art. Transgenic animals which comprise both a regulatory protein and a target regulated promoter/reporter fusion can be created by introducing both components into the same cells at an embryonic stage, or more preferably, an animal which carries nucleic acid sequences encoding one component in its genome is mated to an animal which carries nucleic acid sequences encoding the second component. In one embodiment, a first transgenic animal model containing, in its genome, a nucleic acid sequence encoding a reporter protein operably linked to a regulated promoter to which a regulatable transcription factor binds is mated with a second transgenic animal containing, in its genome, a nucleic acid sequence encoding a regulatable transcription factor operably linked to a promoter which is active in a slow-cycling cell.

Once a cell culture, tissue or transgenic animal has been identified as containing both nucleic acid sequences encoding a regulatable transcription factor operably linked to a tissue-specific promoter and nucleic acid sequences encoding a reporter operably linked to a regulated promoter, the process of identifying and isolating a tissue-specific, slow-cycling cell is initiated. In this step of the method of the invention, the regulatory protein can be activated by the addition of an exogenous stimulus to the cell or organism. Exogenous stimuli including, but not limited to, tetracycline in the Tet-on system, ecdysone, mifepristone, rapamycin, or analogs thereof have been discussed supra. Alternatively, the regulatory protein can already be active in the absence of an exogenous stimulus (e.g., in the Tet-off system). Upon activation, the regulatory protein stimulates expression from the regulated promoter so that reporter protein is accumulated (i.e., the pulse step). Methods of detecting and quantifying reporter protein accumulation are disclosed herein. The time required for this accumulation may be dependent on many factors including the expression vector selected, expression levels from the regulated promoter, expression levels from the tissue-specific promoter, and the stability of the reporter protein.

In the next step of this method of invention, the regulatory protein is inactivated generally by removal of the exogenous stimulus (e.g., in the Tet-on, ecdysone, mifepristone, and dimerizer systems) or addition of an effector molecule (e.g., tetracycline in the Tet-off system). Upon inactivation, expression of the reporter is inhibited or decreased.

Subsequently, the cells are incubated (i.e., chased) for a sufficient amount of time to undergo one or more cell cycles thereby allowing for dilution of the reporter in actively dividing cells. In general, more than two cell cycles are allowed so that in the case of a stem cell, a daughter cell on the path of terminal differentiation divides multiple times. A time sufficient for allowing one or more cell cycles will be dependent on the cell type and species. In general, mammalian cells have a doubling time of approximately 12 hours to several days. Therefore, incubation times can be in the range of two days to two months. In this manner, actively dividing cells can be differentiated from slow-cycling cells by the amount of reporter protein present in the cells (i.e., actively dividing cells will have less reporter protein present compared to slow-cycling cells).

To detect the amount of reporter protein present in a cell the cells from a tissue culture, organotypic culture, or a tissue of interest dissected from a transgenic animal are isolated and reporter activity is measured. Reporter activity can be measured using such methods as flow cytometry, laser confocal microscopy, spectrofluorometer, fluorescence microscopy, immunocytochemistry, western blotting, ELISA, fluorescence scanners, electron microscopy and the like. The reporter activity is then correlated with amount of reporter present in the cell.

Consecutively or concurrently (e.g, when using fluorescence-activated cell sorting), the cells are sorted based on the amount of reporter protein present in each cell. This sorting step is generally carried out using cell-sorting methods such as FACS, hydraulic or laser capture microdissection in combination with laser confocal microscopy or fluorescence microscopy. Cells containing increased levels of the reporter as compared to other cells isolated from the same tissue or culture are deemed tissue-specific, slow-cycling cells.

Having established exemplary markers for bulge stem cells (e.g., β1, α6 integrin, Tcf3, CD34, kit ligand, Dab2, Ephs, Tnc, IL-11 receptor, Idb2, Fh11, Gas, and Bmi-1), as well as other stem cells, two of these markers (i.e., CD34 and alpha 6 integrin) were used to isolate wild-type adult stem cells which are self-renewing and multipotent. Thus, the present invention also relates to a method for isolating a self-renewing, multipotent, slow-cycling cell based on the presence of CD34 and the level of expression of a selected stem cell marker. By way of illustration, the relation between label-retaining cells and their surrounding basal lamina was assessed by conducting a three-dimensional analyses on 40 μm-thick frozen sections of skin from anagen-phase, K5-VP16Tet$^{off}$/TRE-H2B-GFP transgenic mice disclosed herein, fed tetracycline for 5 weeks beginning at one month of age. At this time, only the nuclei of bulge cells retain high levels of H2B-GFP. When sections were counter-labeled with antibodies against α6 integrin, a component of the hemidesmosomes that mediate attachment to the basal lamina (Martin, et al. (2002) supra; Watt (2002) supra), it was evident that although many bulge label-retaining cells contacted this substratum, others appeared to be suprabasal irrespective of image plane. This was most apparent on the side of the bulge where the new hair follicle emerged.

Antibodies against CD34, an established marker of both hematopoietic and skin epithelial stem cells (Ramalho-Santos, et al. (2002) *Science* 298:597-600; Ivanova, et al. (2002) *Science* 298:601-604), stained both basal and suprabasal bulge cells. Antibodies against the typically basal marker K14 as well as a K14-promoter driven GFP-actin transgene also labeled both populations, although suprabasal cells were less bright. Expression of another typically basal keratin, KS, was strong in both compartments. By contrast, the companion layer surrounding the remnant hair shaft was negative for K14 and KS, but strongly positive for the typically suprabasal keratin, K6.

At the end of the first telogen (day 20), the follicle niche was symmetrical, consisting of a single layer of CD34-positive basal cells. As anagen began (~day 22), the suprabasal compartment emerged concomitantly with the bulge. Once formed, both compartments were maintained throughout this and subsequent hair cycles.

To further characterize CD34-positive bulge label-retaining cells, single cell suspensions of skin were subjected to FACS on the bases of H2B-GFP retention and binding to alpha 6 integrin and CD34 antibodies. Two populations of skin epithelial cells retained high H2B-GFP and displayed high surface CD34, but differed in surface alpha 6 integrin. Both pools retained BrdU and were positive for K14-GFPactin. Consistent with immunofluorescence data, alpha 6 integrin low CD34 high (α6LCD34H) cells did not appear until ~day 28, but persisted thereafter. α6LCD34H cells expressed 10× less GFPactin and β1 integrin than α6HCD34H cells. Both expressed outer root sheath markers K5 and K15, but not appreciable differentiation markers for epidermis (K1), companion layer (K6) or IRS (AE15).

When epidermal keratinocytes detach from their underlying basal lamina, they terminally differentiate (Watt (2002) supra). To assess whether the suprabasal status might commit some bulge cells to irreversibly differentiate, potential of these cells to generate keratinocyte colonies in vitro was examined. FACS was used to isolate pure populations of K14-GFPactin expressing α6LCD34H, α6HCD34H, α6LCD34(−), α6HCD34(−) and GFP(+) keratinocytes from postnatal day 28 mouse backskins.

In vitro, primary cultures of these FACS-isolated keratinocytes formed colonies with similar efficiencies. However, only the α6LCD34H and α6HCD34H populations formed appreciable numbers of tightly packed, large colonies (>20 $mm^2$; >$10^4$ cells) containing cells of small size and relatively undifferentiated morphology. Referred to as holoclones, such colonies are clonally derived from single stem cells (Barrandon and Green (1987) *Proc. Natl. Acad. Sci. U S A* 84:2302-2306). Although the number of α6HCD34H-derived holoclones was higher, the ability of α6LCD34H cells to generate holoclones was unexpected given their suprabasal location. By contrast, keratinocytes residing outside the bulge typically generated <5 $mm^2$ colonies, and even larger colonies displayed irregular borders and consisted of bigger, morphologically differentiated cells. The holoclone-forming ability of the FACS-isolated, adult bulge keratinocytes was of interest, in light of the fact that adult mouse keratinocytes have been difficult to culture long-term. In this regard, adult bulge cells resembled newborn and embryonic skin keratinocytes, which form holoclones readily. In addition, the proliferation was greater for cells of the bulge than their epidermal counterparts both in short term and in long-term culture.

To assess the ability of single bulge cells to undergo self-renewal, clonal analyses was conducted by trypsinizing and passaging cells derived from individual holoclones. Cells from representative α6LCD34H and α6HCD34H clones uniquely withstood multiple passages to yield new holoclones, indicating that both bulge populations contain cells that display the morphological and self-renewal features of stem cells when taken outside of their native niche and exposed to proliferation-inducing conditions. The data also indicate that if bulge cells enter early commitment upon detachment from basal lamina (i.e., suprabasal α6LCD34H cells), this process is still reversible, at least in vitro.

Conversely, when keratinocytes derived from each of the two bulge compartments were induced to terminally differentiate in vitro, both populations were able to undergo epidermal differentiation as measured by markers specific for spinous (K1, K10, involucrin) and granular layers (loricrin, filaggrin). Unexpectedly, although relatively rare, some cells were even positive for AE13, specific for hair keratins. This ability was retained even by $9^{th}$ passage cultures. Moreover, it was found that these cells could differentiate into neuronal and glial cells. Upon differentiation with standard medium containing 5% serum supplemented with art established growth factors known to induce neuronal fates in vitro, neuronal and glial cell marker expression, including TuJ (Beta-tubulin III), NF1 (neurofilament) and GFAP (a glial marker), was observed.

It was then determined whether the known ability of bulge cells to give rise to both epidermis and hair follicles is due to multipotency or to the existence of different unipotent bulge stem cell residents. Wild-type newborn mouse keratinocytes can generate epidermis, hair and sebaceous glands if first combined with newborn dermal fibroblasts and then grafted to the back of a nude mouse at a site where the skin has been surgically removed (Lichti, et al. (1993) *J. Invest. Dermatol.* 101:124S-129S; Weinberg, et al. (1993) *J. Invest. Dermatol.* 100:229-236). Nude mice lack hairs because they are deficient for a matrix transcription factor required for hair differentiation (Nehls, et al. (1994) *Nature* 372:103-107; Segre, et al. (1995) *Genomics* 28:549-559). The degree of stem cell self-renewal in vitro enabled the generation of sufficient numbers of K14-GFPactin-positive, α6LCD34H or α6HCD34H keratinocytes derived from single isolated bulge cells to permit such in vivo engraftment studies. Consequently, progeny derived from single GFP-positive holoclones were combined with newborn wild-type dermal cells and the mixture was grafted onto the backs of nude mice.

Grafts of dermal fibroblasts alone were able to produce a dermis that could support the inward migration of nude keratinocytes, which then stratified and terminally differentiated (Lichti, et al. (1993) supra; Weinberg, et al. (1993) supra). Some variability in surface contour was observed, as would be expected from dermal scarring, but the regenerated skin displayed a nude phenotype and lacked a fur coat. By contrast, grafts containing GFP-positive descendants from single α6LCD34H or α6HCD34H bulge cells exhibited tufts of hairs and stretches of epidermis. Fluorescence imaging revealed GFP-positive skin, which extended to, but not beyond, the boundaries of the graft.

Immunofluorescence microscopy of skin sections revealed a marked contribution of GFP-positive bulge descendants within each skin epithelial lineage. The brightest GFP fluorescence was seen in the epidermis, outer root sheath and sebaceous glands where the K14 promoter is most active. Longer exposure revealed GFP fluorescence in the transiently amplifying progenitor cells of the inner root sheath (AE15-positive) and hair shaft, both readily discernable within grafts. Unexpectedly, grafts examined after the completion of their first hair cycle even displayed CD34-positive, K14-GFP-positive cells at the follicle base. Within longer term grafts, evidence of at least one additional round of hair cycling was apparent.

No obvious abnormalities were detected in the morphology of the GFP-positive epidermis, sebaceous glands and hair follicles. Further, GFP-fluorescence was not detected in skin derived from nude or wild-type mice, nor was it detected in non-epithelial cell compartments, e.g., blood vessels or dermis, in which the K14 promoter was not active.

To identify which genes are upregulated in bulge stem cells irrespective of their attachment to basal lamina and regardless of activation state, mRNAs were isolated from FACS-purified bulge populations during resting (7 weeks) and growing (4 weeks) phases of the first postnatal hair cycle and microarray analyses were performed. Individual mRNAs were scored as upregulated if their levels scored >2× relative to the all GFP fraction of keratinocytes. RT-PCR on these and independent samples of fractionated mRNAs validated the quality of the databases.

Consistent with the bulge location of the α6HCD34H and α6LCD34H populations, the list of mRNAs upregulated in either of these compartments encompassed 80-90% of mRNAs found to be upregulated in the bulge genes described herein (Table 1). A significant number of mRNAs were differentially expressed within the bulge, indicating that the attachment to basement membrane markedly influenced the program of gene expression (Tables 2, 3, and 4). Additionally, other mRNAs were upregulated in either telogen or anagen, but not both.

TABLE 2

| | α6LCD34H VS All GFP (Anagen/Telogen) | α6HCD34H vs All GFP (Anagen/Telogen) |
|---|---|---|
| Genes Upregulated | Cdkn1b (P27) (2x/nf) | Cdkn2b (P15) (3x/5x) |
| | Igfbp3 (3x/nf) | Cdknlb (P27) (2x/nf) |
| | Igfbp5 (14x/6x) | |
| | Igfbp6 (5x/6x) | |
| | Igfbp7 (6x/4x) | |
| Genes Downregulated | Cyclin A2 (4x/4x) | Cyclin A2 (9x/5x) |
| | Cyclin B1 (10x/8x) | Cyclin B1 (30x/14x) |
| | Cyclin B2 (9x/5x) | Cyclin B2 (19x/4x) |
| | Cyclin D1 (2x/nf) | Cyclin D1 (nf/7x) |
| | Cyclin D2 (3x/4x) | Cyclin D2 (12x/18x) |
| | Cdc2a (4x/8x) | Cdc2a (27x/13x) |
| | Cdc25c (4x/nf) | Cdc25c (11x/nf) |
| | Cdc6 (3x/2x) | Cdc6 (4x/6x) |
| | Cdc7 (4x/3x) | Cdc7 (6x/4x) |
| | Cdca1 (4x/3x) | Cdcal (13x/11x) |
| | Chek1 (4x/5x) | Chek1 (7x/7x) |
| | Cdkn1a (9x/3x) | Cdkn1a (3x/nf) |
| | Weel (3x/4x) | Weel (3x/5x) |
| | Pcna (2x/2x) | Pcna (2x/2x) |
| | Mki67 (10x/10x) | Mki67 (200x/26x) |
| | Cdkn2b (P15) (2x/nf) | Chek2 (4x/3x) |

*fold changes for either anagen or telogen are indicated in parentheses.
nf denotes not found.

TABLE 3

| | Fold change between α6HCD34H and α6LCD34H (Anagen/Telogen) | Accession No. |
|---|---|---|
| Adhesion and membrane-related proteins | Necl1 (16x/17x) | AF195662 |
| | Sema3e (16x/3x) | NM_011348 |
| | Trpv4 (14x/11x) | NM_022017 |
| | Bgn (13x/nf) | AI931862 |
| | Glrb (9x/5x) | NM_010298 |

TABLE 3-continued

| | Fold change between α6HCD34H and α6LCD34H (Anagen/Telogen) | Accession No. |
|---|---|---|
| | Calcrl (9x/15x) | AF209905 |
| | Itm2a (7x/6x) | BI66443 |
| | Tnfrsfl 1b (5x/3x) | AB013898 |
| | Cspg (5x/3x) | BB377873 |
| | Itb6 (5x/3x) | AK019511 |
| | Alcam (4x/5x) | U95030 |
| | Itm2c (3x/3x) | NM_022417 |
| Growth-related proteins | Ctgf (26x/16x) | NM_010217 |
| | Ltbpl (18x/15x) | AF022889 |
| | Igfbp5 (14x/4x) | BF225802 |
| | Igfbp7 (7x/6x) | AI481026 |
| | Sparc (12x/13x) | NM_009242 |
| | Unc3 (10x/2x) | |
| | Cxcl14 (4x/2x) | AF252873 |
| | Kitl (2x/3x) | BB815530 |
| | Fgfr1 (3x/3x) | M33760 |
| Extracellular Matrix | Col4a1 (10x/6x) | NM_009931 |
| | Col4a2 (10x/6x) | NM_009932 |
| | Col7a1 (7x/5x) | NM_007738 |
| | Col18a1 (2x/nf) | NM_009929 |
| | Vit (14x/8x) | BC019528 |
| | Npnt (5x/7x) | AA223007 |
| | Fbln2 (3x/3x) | AW538200 |
| | Mmp2 (9x/5x) | NM_008610 |
| | S100a4* (5x) | D00208 |
| Transcription | Elav2 (32x/45x) | BB105998 |
| | Irx4 (13x/18x) | NM_018885 |
| | Gli2 (6x/5x) | AW546128 |
| | Scmh1 (3x/2x) | AB030906 |
| Signaling | Ppap2b (5x/6x) | AW111876 |
| Cytoskeleton | Myoc (8x/6x) | AW125804 |

TABLE 4

| | Fold change between α6LCD34H and α6HCD34H (Anagen/Telogen) | Accession No. |
|---|---|---|
| Adhesion and membrane-related proteins | Aqp5 (35x/26x)* | NM_009701 |
| | Pvrl4 (16x/13x) | BC024948 |
| | Pmp22 (8x/8x) | NM_008885 |
| | Ramp1 (4x/16x) | NM_016894 |
| | Nope (3x/2x) | NM_020043 |
| | Sema4g (2x/3x) | NM_011976 |
| Growth-related proteins | Bmp6 (4x/12x) | NM_007556 |
| | Sectm1 (3x/5x) | NM_021401 |
| | FGF-18 (7x/12x) | NM_008005 |
| | Cdkn2b (8x/8x) | AF059567 |
| Extracellular Matrix | Col3a1 (41x/65x)* | NM_009930 |
| | Fbn2 (13x/5x) | NM_010181 |
| | Fn1 (6x/4x) | BC051082 |
| Transcription | Bach2 (3x/3x) | AW553304 |
| | FoxC1 (2x/2x) | BB759833 |
| | Hey1 (31x/18x) | NM_010423 |
| Signaling | Blnk (6x/6x) | AF068182 |
| | Homer2 (4x/4x) | AB017136 |
| Cytoskeleton | Dcamkl1 (43x/21x)* | AW105916 |
| | Sncg (6x/4x) | NM_011430 |
| | Pak3 (5x/3x) | BQ174935 |
| | Kif5c (5x/6x) | AI844677 |
| | Gphn (3x/3x) | AA170590 |

*fold changes for either anagen or telogen are indicated in parentheses.
- Expression levels were determined by RT-PCR for all genes listed.
* indicates that the cell type was specifically identified using an antibody to the protein.

When compared, taking into consideration mRNAs upregulated in both telogen and anagen phases, and in both basal and suprabasal compartments, a short list of key genes defining bulge cell characteristics was determined. This list of 56 upregulated mRNAs provides a molecular signature of bulge cells within their niche (Table 5). Because these genes were upregulated in all bulge stem cell comparisons made, the stem cell niche environment appeared to be more critical to their expression than to attachment to basal lamina or hair cycle stage.

TABLE 5

| | Upregulated mRNAs common to bulge stem cells | Accession No. |
|---|---|---|
| Cytoskeleton | Dmd | NM_007868 |
| | Enah | NM_010135 |
| | Pdlim3 | NM_016798 |
| | Tekt2 | NM_011902 |
| | Sdcbp | AV227603 |
| | Macf1 | BM248206 |
| | Flnb | AW538200 |
| Cell Adhesion/Extracellular Matrix | Itm2a | NM_008409 |
| | Tnc | NM_011607 |
| | Col18a1 | NM_009929 |
| | Col6a1 | NM_009933 |
| | Cd34 | NM_133654 |
| | Igsf4 | NM_018770 |
| | Prlr | NM_008932 |
| Transcription | Peg3 | AB003040 |
| | Idb2 | BF019883 |
| | Fhl1 | U41739 |
| | Idb3 | NM_008321 |
| | Idb1 | U43884 |
| | Ndn | AW743020 |
| | Foxp1 | BG962849 |
| | Dbp | BB550183 |
| Cell Cycle/Growth | Gas1 | BB550400 |
| | Dapk2 | BC022165 |
| | Ptn | BC002064 |
| | Fgf1 | AI649186 |
| Signaling | Dab2 | BC006588 |
| | Plxna2 | NM_008882 |
| | Dkk3 | NM_015814 |
| | Fzd2 | NM_020510 |
| | Gpr49 | BB751088 |
| | Ltbp2 | NM_013589 |
| | Ptprk | AI893646 |
| | Ppap2a | NM_008903 |
| | Fst1 | NM_008046 |
| | Gremlin | NM_011824 |
| Protein/Small Molecule Transport | Kcnk2 | NM_010607 |
| | Sk29a1 | AF305501 |
| | Sk29a8 | NM_026228 |
| | Txn1 | NM_011660 |
| Other | Pole4 | BF577544 |
| | Crip1 | NM_007763 |
| | Lrrfip1 | |
| | Sardh | BI217574 |
| | Ssx2ip | AV075508 |
| | Gcat | AK013138 |
| | Eps8 | NM_007945 |

Further, a subset of mRNAs encoding integral membrane proteins were determined to be upregulated in the bulge and would be useful in isolating bulge-specific stem cells (Table 6).

TABLE 6

| Integral Membrane Protein mRNAs Upregulated in bulge Stem Cells | Accession No. |
|---|---|
| Agpat3 | NM_053014 |
| Adam1a | U22056 |
| Adam9 | NM_007404 |
| Alcam | U95030 |
| Acvrl1 | BC014291 |
| Acvr2b | NM_007397 |
| Aig1 | NM_025446 |

TABLE 6-continued

| Integral Membrane Protein mRNAs Upregulated in bulge Stem Cells | Accession No. |
|---|---|
| Antxr1 | AF378762 |
| Mox2 | AF004023 |
| Aqp3 | AF104416 |
| Aqp5 | NM_009701 |
| Armcx1 | BC021410 |
| Atp8a2 | NM_015803 |
| Atp11a | AV378604 |
| Atp6ap2 | BC014706 |
| Atp1a1 | BC025618 |
| Abca7 | NM_013850 |
| Bcl2l11 | BM120925 |
| Bace1 | BB114336 |
| Boc | BB005556 |
| Bambi | AF153440 |
| Bmpr1a | BM939768 |
| Calcrl | AF209905 |
| Cacna1c | NM_009781 |
| Clstn1 | |
| Comt | NM_007744 |
| Cd81 | NM_133655 |
| Cd24a | NM_009846 |
| Cd34 | NM_133654 |
| Cd47 | AK018679 |
| BC003322 | |
| BC013667 | |
| BC026439 | |
| Ccrl1 | AF306532 |
| Cklfsf3 | NM_024217 |
| Cklfsf8 | BG063249 |
| Cspg4 | NM_139001 |
| Cry2 | BF303057 |
| Cysltr2 | NM_133720 |
| Cyp2s1 | AK004699 |
| Crlf3 | BB161253 |
| Ddx26 | BB381966 |
| Degs | AV286991 |
| D11Ertd18e | AK003278 |
| D14Wsu89e | AA410148 |
| Dfy | AK010883 |
| Enpp1 | AF339910 |
| Egfl6 | NM_019397 |
| Elovl5 | NM_134255 |
| Emb | BG064842 |
| Edg7 | NM_022983 |
| Edg2 | U70622 |
| Edg8 | NM_053190 |
| Efna1 | D38146 |
| Efna4 | NM_007910 |
| Epim | NM_007941 |
| Emp3 | BC001999 |
| F11r | BC021876 |
| Fbxo23 | AI844703 |
| Fgfr1 | M33760 |
| Fkbp1a | AF483488 |
| Flot2 | NM_008028 |
| Fzd2 | BB371406 |
| Fzd3 | AU043193 |
| Fzd7 | NM_008057 |
| Fzd9 | Y17709 |
| Fxyd6 | AB032010 |
| Gpr49 | BB751088 |
| Gabbr1 | BE688087 |
| Gfra1 | BE534815 |
| Grik1 | X66118 |
| Grina | NM_023168 |
| Glrb | NM_010298 |
| Gpm6b | AK016567 |
| Gpc6 | BC023448 |
| Glmr | AB083111 |
| Gas1 | BB550400 |
| Hhip | NM_020259 |
| Hk2 | NM_013820 |
| Has2 | NM_008216 |
| Ier3 | |

TABLE 6-continued

| Integral Membrane Protein mRNAs Upregulated in bulge Stem Cells | Accession No. |
|---|---|
| Igsf4b | AY059393 |
| Itpr3 | NM_080553 |
| Igf2r | BG092290 |
| Itm2a | BI966443 |
| Itgb4 | L04678 |
| Itgb6 | NM_021359 |
| Ifngr2 | BF537076 |
| Ifitm2 | NM_030694 |
| Il11ra1 | BC004619 |
| Jag1 | AA880220 |
| Lancl1 | AJ294535 |
| Leprotl1 | BF658789 |
| Mir16 | BC003902 |
| Mme | AV174022 |
| Map17 | BC013542 |
| Map3k12 | NM_009582 |
| Myadm | BI078799 |
| Marcks | AW546141 |
| Nppc | NM_010933 |
| Nope | NM_020043 |
| Neol | BB667778 |
| Npdc1 | NM_008721 |
| Nptxr | BC019942 |
| Nrp | AK011144 |
| Nisch | BB025231 |
| Notch3 | NM_008716 |
| Odz2 | NM_011856 |
| Odz3 | NM_011857 |
| Pace4 | BI157485 |
| Pcnx | BG073499 |
| Phxr4 | NM_008835 |
| Pmp22 | NM_008885 |
| Ppap2a | NM_008903 |
| Ppap2b | AW111876 |
| Pld2 | NM_008876 |
| Plscr3 | NM_023564 |
| Pttglip | BB498753 |
| Pdgfa | BB371842 |
| Plekha3 | BB780848 |
| Plxna2 | D86949 |
| Plxdc1 | AF378760 |
| Plxdc2 | BB559706 |
| Pvrl4 | BC024948 |
| Kctd2 | AK009318 |
| Kctd4 | NM_026214 |
| Kcnk2 | NM_010607 |
| Kcnma1 | U09383 |
| Kcnma3 | NM_008432 |
| Pappa | AF439513 |
| ank | NM_020332 |
| Prlr | M22958 |
| Procr | NM_011171 |
| Ptpns1 | AB018194 |
| Ptprv | |
| Ptpla | BB014781 |
| Tpst1 | NM_013837 |
| Pcdh20 | BB528056 |
| Pcdhb17 | NM_053142 |
| Pcdhb17 | NM_053142 |
| Pcdhb20 | NM_053145 |
| Pcdhb3 | NM_053128 |
| Pcdhb7 | NM_053132 |
| Pcdhb9 | NM_053134 |
| P2rx4 | AF089751 |
| Ramp1 | NM_016894 |
| Ramp2 | AF146523 |
| Ramp3 | NM_019511 |
| Rga | NM_009057 |
| 0610006O14Rik | NM_133764 |
| 0610027O18Rik | NM_025339 |
| 0910001K20Rik | BM206793 |
| 1110012E06Rik | BM944122 |
| 1110032E23Rik | NM_133187 |
| 1200002N14Rik | BC021433 |

TABLE 6-continued

| Integral Membrane Protein mRNAs Upregulated in bulge Stem Cells | Accession No. |
|---|---|
| 1200007D18Rik | BB095626 |
| 1200013A08Rik | BB765827 |
| 1700001C14Rik | AY047360 |
| 1700019G17Rik | BM214338 |
| 1810017F10Rik | BC019563 |
| 2310016C16Rik | BC019664 |
| 2310028N02Rik | NM_025864 |
| 2310034L04Rik | NM_026417 |
| 2610020H15Rik | AK016023 |
| 2810048G17Rik | NM_133746 |
| 3632451O06Rik | BC023359 |
| 3830613O22Rik | BC019649 |
| 4632428N05Rik | BC003967 |
| 4921511K06Rik | BC006583 |
| 5730403B10Rik | NM_025670 |
| 6330415F13Rik | BC007185 |
| 8430417G17Rik | AV244484 |
| 9130011J04Rik | AK018608 |
| 9130403P13Rik | AK002644 |
| B230339H12Rik | NM_172282 |
| C130076O07Rik | NM_176930 |
| E330036I19Rik | BC016105 |
| Sectm1 | AI481997 |
| Sfrp1 | BB497685 |
| Sema4g | AF134918 |
| Scnn1a | AF112185 |
| Slc12a4 | NM_009195 |
| Slc19a2 | NM_054087 |
| Slc2a3 | NM_011401 |
| Slc20a2 | BB765719 |
| Slc26a2 | NM_007885 |
| Slc29a1 | NM_022880 |
| Slc37a3 | BC005744 |
| Slc37a3 | BC005744 |
| Slc39a13 | BC020106 |
| Slc39a8 | NM_026228 |
| Slc39a8 | NM_026228 |
| Slc4a3 | NM_009208 |
| Slc5a1 | AV371434 |
| Slc6a8 | BG069516 |
| Slc6a6 | NM_009320 |
| Slc7a2 | NM_008478 |
| Sort1 | AV247637 |
| Sorl1 | BI648081 |
| Spry1 | NM_011896 |
| Stim1 | NM_009287 |
| Sdc1 | BI788645 |
| Sdc2 | AU021035 |
| Sdc3 | BB528350 |
| Sdcbp | AV227603 |
| Stx3 | D29800 |
| Stx6 | BQ174465 |
| Thsd1 | AW121720 |
| Tirap | NM_054096 |
| Tgfbr1 | BM248342 |
| Trpm7 | AV320241 |
| Trpv4 | NM_022017 |
| Tm7sf1 | AK009736 |
| Tm7sf3 | AK010720 |
| Tnfrsf11b | AB013898 |
| Tnfrsf1a | L26349 |
| Vps41 | BM240052 |
| Vamp2 | BG871810 |
| Vamp4 | BG065842 |
| Vmd2l1 | BC019528 |
| Zdhhc2 | BB224658 |

By employing a ~2× larger oligonucleotide array than previous bulge analyses, it was determined which upregulated bulge mRNAs were also preferentially upregulated in mRNAs of hematopoietic stem cells (HSCs), embryonic stem cells (ESCs) and neuronal stem cells (NSCs) (Ivanova, et al. (2002) supra; Ramalho-Santos, et al. (2002) supra). Approximately 14% of mRNAs upregulated in HSCs, ESCs and NSCs were also upregulated in either basal or suprabasal bulge stem cells (Table 7).

TABLE 7

| | Upregulated mRNAs common to bulge stem cells, HSCs, ESCs, and NSCs | Accession No. |
|---|---|---|
| Cytoskeleton | Fn1b | NM_010180 |
| | PClo | NM_011995 |
| Cell | Col18a1 | NM_009929 |
| Adhesion/Extracellular | Adam9 | NM_007404 |
| Matrix | Pcdh7 | NM_018764 |
| | Matr3 | BF226671 |
| Transcription | Ndn | AW743020 |
| | Tcf3 | BE994269 |
| | Tcf4 | AI639846 |
| | Fhl1 | U41739 |
| | Zfp354 | NM_011755 |
| | Zfp386 | BC004747 |
| | Mrps31 | NM_020560 |
| | jade1 | AY357298 |
| Cell Cycle/Growth | Ak1 | NM_021515 |
| | Lats2 | BB134767 |
| | Ptov1 | BG073526 |
| Signaling | Ptprk | AI893646 |
| | Trabid | XM_355951 |
| | Stam | NM_011484 |
| | Fzd7 | NM_008057 |
| | Rras | NM_009101 |
| | Trip6 | NM_011639 |
| | Procr | NM_011171 |
| | Socs2 | NM_007706 |
| | Plxdc2 | BB559706 |
| | Maff | BC022952 |
| Protein Modification | Usp2 | AI553394 |
| | Usp9x | AW107303 |
| | Ppp1r2 | BC069886 |
| | Ppic | NM_008908 |
| | Fkbp9 | AF279263 |
| | Cln8 | NM_012000 |
| Protein/Small Molecule | Pkd2 | AF014010 |
| Transport | Fkbp1a | AF483488 |
| | Ttpa | AU019171 |
| | Stxbp1 | AF326545 |
| | Knbp2 | N/A |
| Metabolism | Fut8 | NM_016893 |
| | Gcat | BC024107 |
| | Aldh7a1 | BC012407 |
| Other | Wbp5 | BC007478 |
| | Strn3 | BF148627 |
| | Spg20 | BB040507 |
| | Trim32 | AF230385 |
| | Rga | NM_009057 |
| | Hrsp12 | AK005016 |
| | Rnf138 | AK013419 |
| | Gig1 | NM_133218 |
| | Egln3 | BB284358 |

N/A denotes not available

These comparisons further delineate the short-list of "stemness" genes that now encompasses stem cells isolated from a wide array of tissues. Several genes may play a role in self-renewal and differentiation, including those involved in Wnt signaling (e.g., Tcfs, Fzd7), adhesion (e.g., Cadherin7, Collagen18a1 and Adam9) and transcriptional regulation (e.g., Tcfs, Necdin and Four and a half Lim domain). In contrast, other mRNAs, e.g., that encoding the ABCG2 transporter protein that excludes Hoechst dye 33342 in HSCs and some other stem cells (Zhou, et al. (2001) *Nat. Med.* 7:1028-34) did not appear to be enriched in α6HCD34H bulge stem cells, and was actually down-regulated in the α6LCD34H stem cells. This was consistent with the observation that the CD34(+) bulge stem cells were not enriched by Hoechst dye exclusion, and in this regard differed from HSCs.

Whether in anagen or telogen, both bulge cell populations exhibited reduced mRNA levels for markers of proliferation, such as Ki67 and PCNA, and cell cycle progression, such as cyclins (D2, A2, B1 and B2) (Table 2). Conversely, p27 (cdknlb), an inhibitor of Cyclin E-Cdk2, was upregulated in the bulge relative to the rest of epidermis, as were several members of the IGFBP family (e.g., Igfbp3, 5, 6 and 7), which bind and sequester insulin growth factor, a potent stimulant of epidermal proliferation (Vasioukhin, et al. (2001) *Cell* 104: 605-617; Bennett, et al. (2003) *Development* 130:1079-1088). Thus, the slow-cycling nature of bulge cells appears at least in part to be governed by transcriptional changes, a mechanism not typically implicated in cell cycle control.

To address whether the proliferative status of bulge cells depends upon basal lamina attachment, as it does for basal epidermal cells, BrdU labeling was employed to examine the relative number of S-phase cells in the two compartments of anagen-phase, 4 week-old backskin follicle bulges. FACS analyses revealed fewer BrdU-labeled cells in each of the two bulge populations than in their epidermal counterparts. However, noticeably fewer suprabasal bulge cells were labeled than basal bulge cells. This difference was also seen with longer BrdU pulses and with telogen-phase as well as anagen-phase follicles. These data indicate that bulge cells can proliferate during the hair cycle, but do so to a significantly lesser extent than in the rest of the epidermis. As in the epidermis, basal lamina attachment appeared to influence proliferative status within the bulge.

To assess the history of cell divisions, TRE-H2BGFP/K5Tet$^{off}$ transgenic mice were used to determine how the two bulge populations dilute Histone-GFP protein when expression is shut off for 4 weeks at the start of the first postnatal hair cycle. Both populations were enriched for label-retaining cells when compared to their epidermal counterparts. However, suprabasal bulge cells displayed less fluorescence than basal bulge cells. Together, these data indicate that suprabasal cells undergo more divisions than their basal counterparts, and yet once they enter their suprabasal location, they cycle less frequently. This finding underscores the quiescent state of the niche, and indicates that suprabasal bulge cells may be derived from their basal counterparts.

Accordingly, the present invention further relates to a method for isolating a self-renewing, multipotent, slow-cycling cell based on the presence of CD34 and the level of expression of a selected slow-cycling cell marker. As used herein, a selected slow-cycling cell marker is intended as a marker which has been shown herein to be upregulated in a slow-cycling cell or stem cell of interest. For example, when isolating a slow-cycling cell of the epidermal bulge, it would be desirable to use a cell surface-localized, selected slow-cycling cell marker such as those cell surface-localized proteins provided in Table 5. The subset of membrane-localized, selected slow-cycling cell markers of Table 6 are particularly useful for sorting slow-cycling cells of the epidermal bulge. Further, when sorting a basal from a suprabasal cell (or vice versa) of the epidermal bulge, the selected slow-cycling cell markers of Table 3 and 4 are of particular use and in one embodiment, alpha 6 integrin is desirably used. Moreover, the common stem cell markers of Table 7 can be useful in sorting a stem cell from any tissue or organ. Thus, it is contemplated that the sample from which the population of cells is obtained can be any mammalian tissue or organ which is known to contain slow-cycling cells or stem cells. However, skin is a desirable source of stem cells due to the ease of isolation, suitable availability, and known expression of alpha 6 integrin and CD34 in mouse and human skin (Tani et al. (2000) *Proc. Natl. Acad. Sci. USA* 97:10960-10965; Poblet and Jimenez (2003) *J. Invest. Dermatol.* 121:1220). Methods for obtaining a population of cells from skin samples are described herein and elsewhere and are well-established in the art.

As described herein, CD34 is abundantly expressed on the surface of stem cells and can be used to sort stem cells from surrounding progenitor cells based on the high level of expression of CD34 as compared to the progenitor cells which lack detectable levels of CD34. Exemplary CD34 antibodies which can be used to sort these stem cells, include but are not limited to, those commercially available from ABCAM® (Cambridge, Mass.), BD Biosciences, and Research Diagnostics, Inc. (Flanders, N.J.) or antibodies generated using classical cloning and cell fusion techniques (see, e.g., Kohler and Milstein (1975) *Nature* 256:495-497; Harlow and Lane (1988) Antibodies: A Laboratory Manual, Cold Spring Harbor Laboratory, New York) phage display methods (see, e.g., Huse, et al. (1989) *Science* 246(4935):1275-81). Similarly, CD34-positive cells can be sorted based on the binding to a CD34 ligand (e.g., L-selectin). To facilitate sorting of stem cells, the ligand can be fluorescently labeled according to standard methods or can be attached to a matrix. Sorting of CD34-positive cells can generally carried out using cell-sorting methods such as affinity purification, FACS, hydraulic or laser capture microdissection in combination with laser confocal microscopy or fluorescence microscopy. Alternatively, sorting can be carried out by magnetic separation using BIOMAG® Anti-CD34 antibodies (Polysciences, Inc., Warrington, Pa.).

In contrast to the teachings of Trempus et al. (2003) supra wherein cells were isolated solely on the presence or absence of alpha 6 integrin, this method of the present invention involves sorting the population of cells based on the amount of a selected slow-cycling cell marker, such as alpha 6 integrin, expressed by each cell. When alpha 6 integrin is the selected slow-cycling cell marker, exemplary alpha 6 integrin antibodies which can be used to sort stem cells, include but are not limited to, those disclosed herein or commercially available from R&D Systems Inc. and the like, or antibodies generated using classical cloning and cell fusion techniques. Similarly, alpha 6 integrin-positive cells can be sorted based on the binding to an alpha 6 integrin ligand (e.g., laminin). Methods for using antibodies or ligands for sorting cells is disclosed herein.

In one embodiment, cells having an increased level of alpha 6 integrin expression when compared to the level of expression of the alpha 6 integrin in cells which are reversibly committed to a specified lineage are desirably isolated as these cells exhibit features typical of classical stem cells in that these cells do not exhibit a commitment to a specified lineage. For example, these classical stem cells (also referred to herein as basal cells or α6HCD34H cells) have a 50-fold higher level of alpha 6 integrin protein expressed, as determined by FACS analyses, and a 2-5-fold higher level of alpha 6 integrin mRNA expression when compared to cells which exhibit a reversible commitment to a specified lineage (e.g., suprabasal epidermal bulge cells). Alternatively, these classical stem cells can be isolated or further isolated or identified based on the increased level of expression of one or more upregulated mRNA sequences provided in Table 3. Further, these classical stem cells can be identified by the lack of increased expression in markers associated with cells which are committed to a specified lineage (e.g., markers listed in Table 4).

In an alternative embodiment, cells having a reduced level of alpha 6 integrin expression when compared to the level of expression of the alpha 6 integrin in cells which do not exhibit a commitment to a specified lineage (i.e., classical stem cells) are also useful as these cells are reversibly committed to a specified lineage. For example, these slow-cycling cells (also referred to herein as suprabasal cells or α6LCD34H cells) have a 50-fold lower level of alpha 6 integrin protein expressed, as determined by FACS analyses, and a 2-5-fold lower level of alpha 6 integrin mRNA expression when compared to cells which do not exhibit a commitment to a specified lineage (e.g., basal epidermal bulge cells). Alternatively, these slow-cycling cells can be isolated or further isolated or identified based on the increased level of expression of one or more upregulated mRNA sequences provided in Table 4. Further, these slow-cycling cells can be identified by the lack of increased expression in markers associated with classical stem cells (e.g., markers listed in Table 3).

Despite the impact of the niche, the α6HCD34H and αLCD34H population of cells behave analogously when removed from this location and placed in culture medium and therefore both populations would be therapeutically useful. For example, cultured cells derived from single bulge stem cells from either α6HCD34H or α6LCD34H were able to produce epidermis, hair follicles and sebaceous glands in engraftments. Thus, despite the substantial differences in gene expression underlying these two populations in vivo, the cells nevertheless retained their potential to become bonafide stem cells after passaging in vitro and grafting in vivo.

The results of the experiments provided herein further show that FGF-18 and BMP-6, two of only three mRNAs encoding ligands that were substantially upregulated in suprabasal bulge cells, contribute to the growth inhibitory state of bulge cells. FGF-18 transcript levels were also higher overall within the bulge than outside this niche. Since both bulge populations expressed mRNAs encoding their corresponding membrane receptors, it was examined how primary bulge keratinocyte colonies respond to these factors.

Both FGF-18 and BMP-6 inhibited growth of all keratinocytes tested, irrespective of location within skin epithelium (Table 8). The inhibitory effects occurred in a dose-dependent fashion (Table 9 and Table 10), and cell cycle profiles showed an S-phase reduction in the treated cultures; 10.75% of untreated cells were in S-phase whereas 8.7% or 5.43% of cells treated with FGF-18 or BMP-6, respectively, were in S-phase. Despite signs of reduced proliferation, the effects were reversible and appreciable terminal differentiation was not induced, as judged by colony morphology and biochemical markers. When taken together with the upregulation of TGFP pathway members in the bulge, these data provide new insights into mechanisms by which the specialized, reversible growth inhibitory environment of the bulge can be generated.

TABLE 8

| Population of | Relative Number of Cells | | |
|---|---|---|---|
| Cells | Control | FGF-18 Treated | BMP-6 Treated |
| All GFP | 1 | 0.36 | 0.17 |
| α6LCD34- | 1 | 0.28 | 0.11 |
| α6HCD34- | 1 | 0.37 | 0.14 |
| α6LCD34H | 1 | 0.30 | 0.14 |
| α6HCD34H | 1 | 0.54 | 0.16 |

TABLE 9

| BMP6 Concentration (ng/mL) | Number of Cells |
|---|---|
| 0 | $1.23 \times 10^5$ |
| 50 | $1.31 \times 10^5$ |
| 100 | $1.13 \times 10^5$ |
| 200 | $6.98 \times 10^4$ |
| 400 | $4.28 \times 10^4$ |

TABLE 10

| FGF-18 Concentration (ng/mL) | Number of Cells |
|---|---|
| 0 | $1.23 \times 10^5$ |
| 10 | $1.26 \times 10^5$ |
| 20 | $1.13 \times 10^5$ |
| 40 | $9.07 \times 10^4$ |
| 80 | $6.86 \times 10^4$ |

Thus, the present invention also relates to a method for inhibiting the growth of a selected cell. The method involves contacting a selected cell, either in vivo or in vitro, with an effective amount of BMP6 or FGF-18 to inhibit the growth of the cell. As Sectml was also found to be specifically upregulated in the suprabasal cells, it is contemplated that this growth factor would also be useful in inhibiting the growth of a selected cell so that it will cycle more slowly.

While the present invention discloses growth inhibition of mouse keratinocytes irrespective of location within skin epithelium, it is contemplated that this method will be generally applicable to cells from other species and tissues. Accordingly, a selected cell is intended to include a keratinocyte as well as a cell from any other tissue or organ. An effective amount of BMP6 or FGF-18 is an amount which reversibly inhibits growth of the cells contacted with BMP6 or FGF-18 and can be assessed by standard methods including cell counts, spectrophotometric changes in optical density and the like. This amount can be in the range of 1 ng/mL to 10 μg/mL, 1 ng/mL to 500 ng/mL or 200 ng/mL to 500 ng/mL.

BMP6 and FGF-18 can be obtained by purifying the proteins from cells which naturally express BMP6 or FGF-18 or can be recombinantly produced in prokaryotic or eukaryotic cells using standard, well-established methods. For example, BMP6 and FGF-18 can be expressed in bacterial cells such as *E. coli*, insect cells (e.g., in the baculovirus expression system), yeast cells or mammalian cells using commercially available reagents and methods. Suitable host cells are discussed further in Goeddel (1990) Gene Expression Technology: Methods in Enzymology 185, Academic Press, San Diego, Calif. Examples of vectors for expression in yeast *S. cerevisiae* include pYepSecl (Baldari, et al. (1987) *EMBO J.* 6:229-234), pMFa (Kurjan and Herskowitz (1982) *Cell* 30:933-943), pJRY88 (Schultz, et al. (1987) *Gene* 54:113-123), and pYES2 (INVITROGEN Corporation, San Diego, Calif.). Baculovirus vectors available for expression of nucleic acids to produce proteins in cultured insect cells (e.g., Sf 9 cells) include the pAc series (Smith, et al. (1983) *Mol. Cell. Biol.* 3:2156-2165) and the pVL series (Lucklow and Summers (1989) *Virology* 170:31-39).

The addition of factors such as FGF-18 and BMP-6, having the ability to slow cell growth without inducing terminal differentiation, provides a way to place stem cells in a holding pattern, able to maintain a quiescent state and yet still primed to respond to growth and/or differentiation cues imposed by changes in the microenvironment.

Having demonstrated that a common set of mRNAs are upregulated in HSCs, ESCs and NSCs and in either basal or suprabasal bulge stem cells, markers are provided for identifying multipotent, slow-cycling cells (see, Table 7). Detection of these markers can be carried out using any standard method for detecting a protein or mRNA sequence. For example, proteins can be detected by contacting a cell with a binding agent (e.g., an antibody or aptamer) which binds the marker and a resulting stem cell marker-binding agent complex is washed, to remove non-specific binding, and detected using standard assays (e.g., an immunoassay). When the binding agent is, for example, a peptide aptamer, the binding agent-antigen complex can be directly detected by, for example, a detectable marker protein (e.g., β-galactosidase, GFP or luciferase) fused to the aptamer.

Alternatively, expression of the marker is detected via the of presence the marker mRNA using methods such as northern blot analysis, reverse-transcriptase PCR, microarray analysis and the like. Due to the ease of use, it is generally desirable to detect the mRNA sequences using a PCR-based approach. In general, this involves contacting a cell sample with two or more PCR primers which specifically hybridize with nucleic acid sequences encoding the stem cell marker or which flank the coding region of the stem cell marker, subjecting the sample to multiple steps of PCR amplification and detecting the presence or absence of the amplified sequence (e.g., using gel analysis, blotting methods, or fluorescently-labeled primers). Alternatively, an oligonucleotide, an aptamer, a cDNA, an antibody, or a fragment thereof, which interacts with at least a portion of the nucleic acid sequence encoding the stem cell marker is configured in an array on a chip or wafer and used for detecting nucleic acid sequences encoding the stem cell marker. Primers or oligonucleotides for use nucleic acids encoding a marker can be selected from any region of the locus encoding the marker and generally specifically anneal and amplify at least a portion of nucleic acid sequences encoding the marker and no other nucleic acid sequences encoding a closely related marker. In general, the primers are 12 to 30 bp in length and generate a PCR amplicon of 50, 100, 200 400, 600, 1000 bp or more in length. The fundamentals of non-degenerate PCR are well-known to the skilled artisan, see, e.g. McPherson, et al., PCR, A Practical Approach, IRL Press, Oxford, Eng. (1991).

The methods of the present invention are particularly useful in isolating slow-cycling cells of mammalian origin (e.g., human, mice, rats, pigs, cows, dogs, and the like). In addition, it is contemplated that the slow-cycling cells isolated in accordance with the methods of the invention would be useful in human tissue culture and organotypic culture systems wherein the slow-cycling cells are isolated from normal or diseased human tissues or organs.

Advantageously, using the sorting methods disclosed herein a single, individual stem cell can be isolated and cultured under appropriate conditions to generate a clonal population of cells expressing markers specific to the stem cell and exhibiting the characteristics of self-renewal and multipotency.

Once isolated, a slow cycling cell of the present invention can be maintained in culture and expanded in an undifferentiated state in accordance with the conditions disclosed herein. Such conditions for generating a clonal population of multipotent cells involves incubating an isolated multipotent, slow-cycling cell in the presence of about 0.2 mM to 0.5 mM calcium and a thick layer of fibroblast cells which function as feeder cells. It was found that the combination of a single, high density layer of contact-inhibited, mitotically inactive fibroblasts and a reduced level of calcium in the medium allowed for expansion of the selected multipotent, slow-cycling cells isolated herein. As the fibroblasts age, it can be desirable to replace old fibroblast cells with new fibroblasts within the first week of plating the isolated multipotent, slow-cycling cell. When individually isolated stem cells are placed on this combination of fibroblasts and calcium in a standard medium base, individual colonies of clonal cells (~10,000 cells/colony) can be isolated.

While the present invention discloses culture conditions for generating a clonal population of stem cells isolated from the epidermal bulge, it is contemplated that this method will be generally applicable to epidermal bulge cells from other species as well as other stem cells isolated from other tissues. Accordingly, a selected, multipotent, slow-cycling cell is intended to include a bulge stem cell, hematopoietic stem cell, embryonic stem cell and neuronal stem cell.

Slow-cycling cells isolated and maintained in accordance with the methods disclosed herein are contemplated as being useful in tissue regeneration and repair (e.g., hair regrowth) by grafting said cells to an animal in need of treatment, the treatment of a broad range of diseases, and basic research to understand the properties of adult stem cells and their ability to divide and differentiate along different lineages. Using methods described herein, and those well-known in the art, the stem cell compositions of the present invention can be differentiated into various cells of the epidermis, and central and peripheral nervous system, and the like. Identification of a differentiated cell can be carried out using markers known to be expressed by the cell type of interest and such markers are generally known to the skilled artisan.

Further, as exemplified herein, stem cell-specific markers can be identified which will be useful in the determination of the molecular basis for specific diseases originating from the impairment of stem cell function. Moreover, isolated stem cells or clonal populations thereof, can be used for drug and pharmacological design and screening purposes. The invention is described in greater detail by the following non-limiting examples.

EXAMPLE 1

Transgenic Mice and H2B-GFP Label and Chase

To express H2B-GFP transiently in mice, the tetracycline inducible system was used. The tet-on system is known for its quick up-regulation of the transgene of interest upon induction, with undesired low levels of leaky expression, while tet-off is known to be undesirably slow in up-regulating expression, but provides a tight control of transgene expression (i.e., no leakiness). Thus, it was desirable to use the tet-off system for the studies conducted herein.

To insert the H2B-GFP transgene under the control of the TET response element (pTREH2BGFP vector), a 1 kb DNA fragment containing the H2B-GFP gene was obtained by restriction enzyme digest of pBOS-H2BGFP vector (BD Bioscience, Palo Alto, Calif.) with SalI/NotI. The fragment was ligated into the multiple cloning site of pTRE2 vector (CLONTECH™, Palo Alto, Calif.). A linear fragment generated by digestion with XhoI/SapI was purified and transgenic CD1 mice were generated using well-known methods (Taylor et al. (2000) supra).

For a control, a K14-H2BGFP fusion was generated, in order to verify that strong expression of H2B-GFP did not affect the reproductive viability or physiology of the mice. To engineer this vector, the H2BGFP insert was cut from the pBOS-H2BGFP vector with SalI, followed by blunting the ends, and cutting with XbaI. The 1.1-kb fragment was inserted in the K14βGlobincasseteCOR2R (Vasioukhin et al. (1999) supra) that was linearized with BamH1, blunted, and cut with XbaI. The vector was then linearized with SacI and SphI (New England Biolabs, Beverly, Mass.) and the 4.2-kb fragment was used to create transgenic K14-H2BGFP mouse lines.

Twenty transgenic mouse lines harboring the pTRE-CMV-H2B-GFP transgene were generated and subsequently screened. One mouse was selected that showed no expression in the skin. In addition, in some of the 20 founder mice, low levels of constitutive expression were detected in a very small fraction of cells scattered in the dermis, in the subcutis (below the dermis) and in the tailbone, but no expression in the hair follicle and the epidermis.

To screen through these 20 founder mice and find one that was inducible, fibroblast lines from tails of 21 day-old founder mice were generated and tested for induction using transfection of a CMV-tetVP16 construct. The rational was that an insertion site not inducible in fibroblast might be un-inducible also in other cell types, (e.g., keratinocytes) due to possible insertion of the pTRE-H2BGFP transgene into sites of permanently silenced chromatin. Five fibroblast inducible founders were selected and mated with transgenic mice harboring the K5-tetVP16 transgene. Double transgenic mice pTRE-H2BGFP/K5-tetVP16 derived from three founder pTRE-H2B-GFP mice showed high levels of fluorescence in the epidermis and the hair follicle.

To assess whether all the H2B-GFP signal at the end of the chase was due to long-lived, stable protein, or if there was any leaky expression in the presence of doxycycline (when the transgene should be shut off), a double transgenic mice pTRE-H2BGFP/K5-tetVP16 was generated, wherein expression of the transgene in the early embryo was prevented by feeding the pregnant mothers doxycyline 2 g/kg chow (BIO-SERV®, Frenchtown, N.J.). Feeding was initiated starting at E 9.5, before the KS promotor became active (it is well established that doxycycline traverses the placenta and is also present in the mother milk). Therefore, any expression of the transgene in these young pups would be due solely to leakiness of the tet-off system. Double transgenic mice born of this litter (3 pups double positive) were completely dark, with no GFP detected in the hair follicle or the epidermis, demonstrating complete suppression of the transgene by doxycyline administration.

Withdrawal of doxycycline resulted in recovery of H2BGFP expression first in the outer root sheath and epidermis (2 weeks after withdrawal), with no initial signal in the hair follicle matrix. Complete full brightness in mouse skin epithelium (similar in levels with double transgenic mice in the absence of any doxycycline feedings) was achieved approximately 4 weeks after doxycycline withdrawal. This demonstrated that the tet-off driven H2B-GFP system was not leaky and that doxycycline completely suppressed expression in the hair follicle and the epidermis. In all the cell isolation experiments described herein, small pieces of skin were collected from three body regions of the animals and OCT sections were analyzed under the fluorescence microscope (Zeiss confocal microscope). Although bulge cells were always the brightest cells in the skin, an occasional mouse with appreciable GFP in the epidermis was found. Such animals were not used for experiments, and mice were always prescreened for faithful and quantitative H2B-GFP chase prior to embarking on analyses/experimentation.

To analyze the decay of the H2B-HGP signal, double transgenic mice were fed doxycycline starting 6 days, or more frequently, at 4 weeks post-natal and were kept on doxycycline food for the entire time of the chase (4-16 weeks). The GFP fluorescence markedly decreased after 1 week of chase and continued to be lost progressively during the 4-8 week period, concomitant with expected cell divisions. When doxycycline feeding was initiated at 6 days postnatally, fluorescence was very low after 13 weeks of chase, but was still detectable upon overexposure. When doxycycline was initiated at 4 weeks of life, label-retaining cells could easily be detected 4 months after the chase. This demonstrated that in vivo, label-retaining cells are long-lived.

5-Bromo-2'-deoxyuridine (BrdU) (Sigma-Aldrich, St. Louis, Mo.) pulse-chase experiments were performed as described (Braun et al. (2003) *Development* 130(21):5241-55). Postnatal, day 10, CD-1 mice were injected intraperitoneally with 50 μg/gram BrdU 2×/day for 2 days and analyzed 28 days later (chase period) for label retention. For cell cycle analysis, day 28 mice were injected once with 50 μg/gram BrdU and analyzed 4 hours later for BrdU incorporation. Continuous BrdU administration was performed by adding BrdU to drinking water at a concentration of 0.8 mg/mL.

EXAMPLE 2

Immunofluorescence

Tissues for immunofluorescence and Hematoxylin and Eosin staining were embedded in OCT and then frozen immediately on dry ice. OCT sections were fixed for 20 minutes in 4% paraformaldehyde (PFA) in phosphate-buffered saline (PBS) and washed 3 times for 5 minutes in PBS. The PFA-free sites were blocked using glycine (20 mM). When staining with mouse monoclonal antibodies, the reagents and protocol used from the M.O.M.™ Basic kit (Vector Laboratories, Burlingame, Calif.). Alternatively, the following block/diluent: 2.5% normal donkey serum, 2.5% normal goat serum, 1% bovine serum albumin, 2% gelatin and 0.1% TRITON® X-100 (Sigma-Aldrich, St. Louis, Mo.) in PBS. The primary antibodies at the indicated dilutions were KS. (Guinea Pig, 1:300); K15 (Rabbit, 1:1000; chicken 1:100); K19 (Rabbit, 1:1000); K1 (Rabbit, 1:200); K6 (Rabbit, 1:1000), β1 integrin (Rat, 1:50; CHEMICON®, Temecula, Calif.); β4 integrin (Rat, 1:100; PharMingen, San Diego, Calif.); α6 integrin (Rat, 1:50; PharMingen); β6 integrin (Rabbit, 1:5); Ki67 (Rabbit, 1:1000; NovoCastra Laboratories, Newcastle, UK); phospho-H3 (Rabbit, 1:150; Upstate Cell Signaling, Liake Placid, N.Y.); CD34 (Rat, 1:50 or 1:100; BD Biosciences); P-smad2 (Rabbit, 1:100; Cell Signaling, Beverly, Mass.); Dab2 (Rabbit, 1:400); Tektin2 (Rabbit, 1:200-400); basonuclin (1:100); S100 A6 (Rabbit, 1:100, NovaCastra Laboratories); S100 A4 (Rabbit, 1:500, Basic Research Laboratories, Kanebo, Ltd.); Tenascin C (Rabbit, 1:200; CHEMICON®); Ephrin-B1 (Goat, 1:5, R&D Systems, Minneapolis, Minn.); EphA4 (Goat, 1:5; R&D Systems); EphB4 (Goat, 1:5; R&D Systems); LTBP1 (rabbit, 1:200); Left (rabbit, 1:200); GATA3 (mouse, 1:100, Santa Cruz Biotechnologies, Santa Cruz, Calif.); AE13 (mouse 1:10); BrdU (Rat, 1:50 , Abcam); Dcamkll (Rabbit, 1:300);. For FACS analysis, antibodies to cell surface marker epitope and CD34 and CD71 coupled with biotin (BD Biosciences) were used. Secondary antibodies were either IgGs of the appropriate species (e.g., anti-donkey or anti-goat antibodies; 1:300), or avidin for the biotinylated antibodies, and were coupled with TexasRed for immunofluorescence (Jackson Laboratories, Bar Harbor, Me.) or with phycoerithrin (PE) (Rockland, Gilbersville, Pa.), APC (Rockland) for FACS analysis or FITC.

Nuclei were stained using 4'6'-diamidino-2-phenylindole (DAPI) for immunofluoresence and TOPRO-3 (Molecular Probes) for confocal microscopy. Three dimensional reconstructions of confocal analysis were performed using LSM510 Confocal Analyzer (Zeiss) or IMARIS softwares (Bitplane AG).

EXAMPLE 3

Cell isolation, FACS Sorting, and RNA Sample Preparation

Total skin from adult mice was gently scraped with a scalpel to remove fat and underlining subcutis. For cell isolation using cell surface markers, K14-GFPactin mice were used. Skin was then subjected to enzymatic digestion with collagenase and 0.25% trypsin. Following neutralization with ice-cold Dulbecco's Modified Eagle Medium supplemented with 15% fetal bovine serum (FBS) (Sigma-Aldrich), cells were strained (70 μM, then 40 μM pores; BD Bioscience) and kept on ice for all the subsequent steps of the procedure.

Single-cell suspensions from total skin were either analyzed or sorted. For sorting, single cell suspensions in 2% FCS in phosphate-buffered saline (PBS) were then exposed for 30 minutes on ice to primary antibodies directly coupled with a fluorochrome or with avidin. After washing 2 times with PBS, cells were incubated with Streptavidin coupled to specific fluochromes (1:200, Pharmingen) for 30 minutes, and then washed and resuspended in PBS supplemented with 2% FCS and 300 ng/mL propium iodide (Sigma-Aldrich).

For sorting by cell surface marker expression, primary antibodies used for FACS analysis were anti-α6 integrin (CD49f) directly coupled to FITC, PE or Cychrome (Pharmingen) and anti-CD34 coupled to biotin, FITC, or PE (Pharmigen), anti-α1 integrin-biotinylated (Pharmingen). BrdU detection was performed using BD Pharmingen BrdU Flow Kit (Pharmingen). Cell isolations were performed on a FACS-VANTAGE™ SE system equipped with FACS DiVa software (BD Biosciences). Epidermal cells were gated for single events and viability, then sorted according to their expression of K14-actin GFP, α6-integrin and CD34. Purity of sorted cells was determined by post-sort FACS analysis and typically exceeded 95%. FACS analyses were performed either on FACSort or BD LSR (BD biosciences). Cytospin analysis was done with a Cytospin4 unit (Thermo/Shandon), and stained as described herein.

For cell cycle analysis, $1.2\times10^5$ cells of the $GFP^{high}$, $GFP^{low}$, and total skin cells were isolated by flow cytometry, pelleted and resuspended in 0.4 μl of cold 70% ethanol. Ethanol-fixed cells were pelleted, washed once in PBS, and stained with a solution propidium iodide (20 μg/ml)—RNAse (250 μg/ml) for 30 minutes at 37° C. Propidium iodide stained cells were analyzed using a FACSCALIBUR™, with an initial gate set on a propidium iodide area (FL2-A) versus width dot plot (FL2-W) for doublet discrimination. $2.5\times10^4$ cells were examined for each sample. Margins for the G2/M peak were set according to the Geometric mean of the G0/G1 peak and analyzed using CELLQUEST™ software.

For RNA sample preparation, 100,000 cells/mouse/fraction of the $GFP^{High}$, $GFP^{Low}$ and β4-fraction populations from 8 week-old (4 weeks of chase) mice were sorted and collected directly into RNA lysis buffer. Duplicate samples were matched by age, sex, and duration of chase. Total RNAs from $GFP^{High}$, $GFP^{Low}$ and β4 positive FACS-sorted cells were extracted and their quality was verified by Agilent RNA 6000 Nano LABCHIP® kit (Agilent) and the concentration was determined by RIBOGREEN® RNA quantitation kit (Molecular Probes, Eugene, Oreg.).

EXAMPLE 4

Cell Culture

Viability of FACS-isolated adult keratinocytes was assessed by Trypan Blue (Sigma) staining and cell numbers were determined by hemocytometer. Equal numbers of live cells were plated onto mitomycin-treated 3T3 fibroblasts in E-Media (Rheinwald and Green (1977) *Nature* 265:421-424) supplemented with 15% serum and approximately 0.3 mM calcium. After 14 days in vitro, cells were trypsinized and counted (Coulter Counter; Beckman). To visualize colony number and morphology, cells were stained with 1% Rhodamine-B (Sigma). For immunofluorescence, FACS-isolated cells were plated onto chamberslides. For expansion of particular colonies, individual holoclones were trypsinized in cloning cylinders and passaged onto a fresh fibroblast feeder layer. To induce terminal differentiation, serum was reduced to 5% and calcium was raised to 1.5 mM.

EXAMPLE 5

Engraftment Experiments

Engraftments were performed according to established methods (Weinberg (1993) *J. Invest Dermatol.* 100(3):229-36). Equal numbers of newborn dermal fibroblasts±K14-GFPactin epithelial cells (α6LCD34H or α6HCD34H) were combined at $10^4$ cells/μL, and 500 μL were injected into a silicon chamber implanted onto the back of an anesthetized nude mouse (Jackson Laboratories). After 1 week, wounds had healed and chambers were removed. Hair typically appeared 1-2 weeks thereafter.

EXAMPLE 6

Transcriptional Profiling of Transgenic Mice pTRE-H2BGFP/K5-tetVP16

Equal amounts of RNA (150 ng) from duplicate samples (each an individual mouse; $10^5$ cells/sample) were amplified using the RIBOAMP™ OA RNA Amplification Kit (Arcturus, Mountain View, Calif.), which ensures linear amplification of individual mRNAs. Biotin labeling of the amplified RNA was done using the BIOARRAY™ HIGHYIELD™ RNA Transcript Labeling kit (T7) (Enzo Life Sciences, Farmingdale, N.Y.). Eight micrograms of biotin-labeled cRNA was fragmented for 35 minutes at 94° C. in fragmentation buffer (AFFYMETRIX, Santa Clara Calif.) for each sample. AFFYMETRIX high-density oligonucleotide arrays for mouse (MG-U74Av2 containing 12,000 probes) were stained and washed according to the manufacturer's protocol.

Scanned chip images were analyzed with the AFFYMETRIX Microarray Suite MAS 5.0. (AFFYMETRIX, Santa Clara, Calif.). Chip files were generated with batch analysis for expressions using the following parameters for all probe sets: target signal scaling 150; Alpha1 0.04; Alpha2 0.06, Tau 0.015, Gamma2L 0.0003, Gamma 2H0.003, Perturbation 1.1. $GFP^{High}$ was the input file and the baseline was either $GFP^{Low}$ or β4 positive. The chip files generated were processed using AFFYMETRIX MicroDB and Data Mining Tools software (AFFYMETRIX) that used a statistical algorithm to calculate p values for each individual probe signal and assessed a present absent call based upon a p value of less than 0.04, and a change call (increased, decreased, and not changed) between input and baseline based upon a change p value of less than 0.025. The 154 probes enriched in bulge label-retaining cells versus basal layer/outer root sheath fulfilled the following criteria: i) they were called present (P) in both GFP-High samples (2 in 2); ii) they were called increased in 4 out of 4 comparisons [GFP-High vs GFP-Low (mouse 1), GFP-High vs GFP-Low (mouse 2) and 2), GFP-High vs B4 fraction (mouse 1) and GFP-High vs B4 positive fraction (mouse 2)]; iii) the average signal log ratios was ≧1 (a fold change minimum of 2).

EXAMPLE 7

RNA Isolation and Microarray Analysis of CD34/α6 Integrin-Positive Cells

Cells were collected from FACS into lysis buffer, and total RNAs were purified using the ABSOLUTELY RNA® kit (STRATAGENE). mRNAs were assessed by RNA 6000 Pico Assay (Agilent) and quantified spectrophotometrically. Primer olig0-dT-T7 (Genset) was used to reverse transcribe (SUPERSCRIPT™ cDNA synthesis kit; INVITROGEN), and then amplify (MESSAGEAMP™ aRNA kit, AMBION) 200 ng RNAs. Random priming and biotinylated nucleotides were used to obtain cRNA for microarray. After quality control (AGILENT), 10 μg labeled cRNA was hybridized for 16 hours at 45° C. to mouse genome array MOE430a (AFFYMETRIX). Processed chips were then read by an argon-ion laser confocal scanner (Genomics Core Facility, MSKCC). The entire procedure was repeated in duplicate for each sample to produce two independent datasets per mRNA sample.

Raw microarray images were quantified using Gene Chip Operating Software (GCOS, AFFYMETRIX). The default analysis parameters and a target value intensity of 500 were employed. Results were then filtered to eliminate any change calls below 2× (p value >0.01). Gene changes scored as increasing but called absent in the numerator, and any changes scored as decreased and called absent in the denominator were eliminated. Gene changes were confirmed by analyses of duplicate arrays. For comparative purposes, MOE430a probe sets were converted to equivalent probe sets on MGu74V2 AFFYMETRIX arrays (MGu74V2A,B,C, 36,000 probe sets), employing GENESPRING® (Silicon Genetics). Since only 22,000 probe sets could be directly compared, the common upregulated probe sets may under-represent the actual overlap for databases acquired with larger probe sets.

EXAMPLE 8

Semi-Quantitative RT-PCR

Reverse-transcription reactions (RT) were performed using total RNA, random hexanucleotides, and SUPERSCRIPT™ II reverse transcriptase (INVITROGEN™, Life Technologies, Rockville, Md.) according to standard procedures. Concentrations were determined using RIBOGREEN®. All the RT reactions were diluted at 0.15 ng/μl and 1 μl of each RT was used for semi-quantitative PCR and a GAPDH or HPRT control for equal loading was used throughout the experiments. PCR amplification of sample targets was completed using primers designed to produce a product spanning exon/intron boundaries. Control amplifications with RNAs minus reverse transcriptase yielded no products for any of the primer pairs tested.

What is claimed is:

1. A method for isolating a self-renewing, multipotent, slow-cycling cell comprising obtaining a population of cells from a sample and sorting the population of cells based on the presence of CD34 and the amount of a selected slow-cycling cell marker expressed by each cell, so that a self-renewing, multipotent, slow-cycling cell is isolated, wherein the selected slow-cycling cell marker is selected from the group of Transcription Factor 3, Transcription Factor 4, Alpha 6 Integrin, G-Protein-Coupled Receptor 49 and Bone Morphogenetic Protein Receptor 1A.

* * * * *